Figure 1:
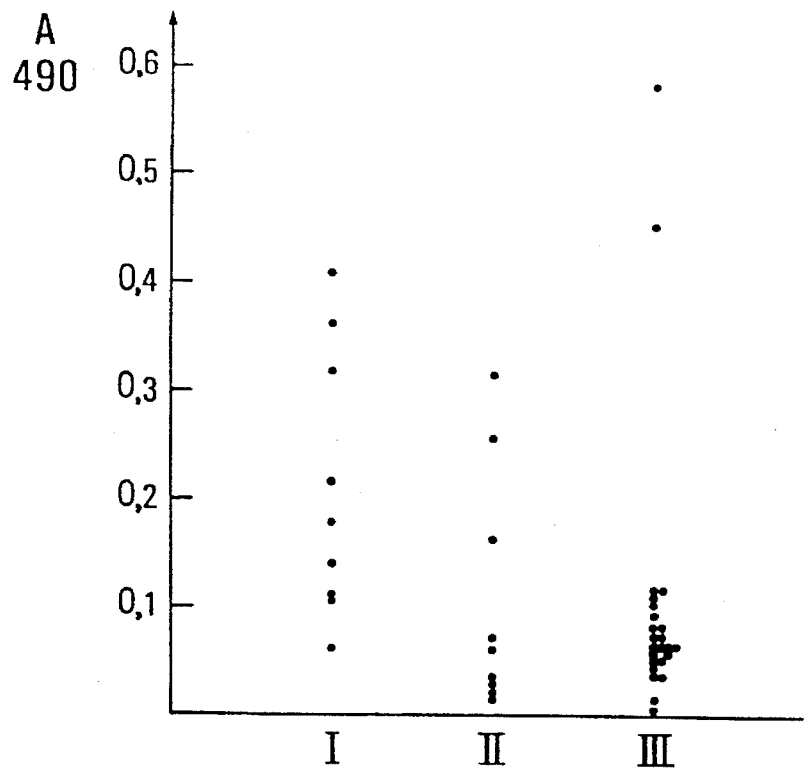

United States Patent [19]

Dillner et al.

[11] Patent Number: 5,629,146
[45] Date of Patent: May 13, 1997

[54] METHOD FOR DETECTION OF HUMAN PAPILLOMAVIRUS (HPV) FOR DIAGNOSTIC PURPOSES

[75] Inventors: Joakim Dillner; Lena Dillner, both of Stockholm, Sweden

[73] Assignee: Ferring AB, Malmo, Sweden

[21] Appl. No.: 678,974

[22] PCT Filed: Oct. 30, 1990

[86] PCT No.: PCT/SE89/00612

§ 371 Date: Jun. 25, 1991

§ 102(e) Date: Jun. 25, 1991

[87] PCT Pub. No.: WO90/04790

PCT Pub. Date: May 3, 1990

[30] Foreign Application Priority Data

Oct. 28, 1988 [SE] Sweden .................................. 8803870

[51] Int. Cl.$^6$ .................................................. C12Q 1/70
[52] U.S. Cl. ...................... 435/5; 435/7.92; 436/513; 436/518; 436/813
[58] Field of Search ........................ 435/5, 7.9, 7.1, 435/7.2, 7.92; 530/387, 388, 326, 327; 436/348, 808, 514, 515, 516, 513, 518, 813; 424/86, 89, 93

[56] References Cited

U.S. PATENT DOCUMENTS

| | | | |
|---|---|---|---|
| 4,748,109 | 5/1988 | Baird | 435/5 |
| 4,777,239 | 10/1988 | Schoolnik et al. | 530/326 |

FOREIGN PATENT DOCUMENTS

| | | |
|---|---|---|
| 16464/83 | 2/1984 | Australia . |
| 30071/84 | 8/1986 | Australia . |
| 0243221 | 10/1987 | European Pat. Off. . |
| 0257754 | 3/1988 | European Pat. Off. . |
| 0235187 | 12/1991 | United Kingdom . |
| WO86/02930 | 5/1986 | WIPO . |
| WO86/05816 | 10/1986 | WIPO . |
| WO87/01375 | 3/1987 | WIPO . |

OTHER PUBLICATIONS

Firzlaff, J.M. et al. "Detection of HPV Capsidantigen in Various Squamous Epithelial Lesions using Antibodies Directed against L1 & L2" *Virol.* 164:467–77 (1988).

Kirsch, I. et al., "Demonstration of SC, IgA, IgG, IgM by Peroxidase—antiperoxidase Technique in Inverted Papillomas of Nasal Cavities", *Human Pathol.* 15(10):915–20 (1984).

Li et al., Identification of the Human Papillomavirus Type Bb L1 Open Reading Frame Protein in Condylomas and Corresponding Antibodies in Human Sera. Journal of Virology B1(9):2684–2690, 1987.

Li, Chemical Abstracts, 107:130590f, p. 395, 1987.

Medline NLM 87093933 Scand. J. Dent. Res, Oct. 1986, 94(5), pp. 419–426. (Abstract).

Medline NLM 86243722 Breast Cancer Res. Treat. 1986, 7(2), pp. 97–103. (Abstract).

Medline NLM ICDB/85005993 Second General Meeting of the Int. Assoc. or Oral Pathol. Jun. 4–7, 1984, meeting abstract.

Doorbar, Chem. Abstr., vol. 107:130591g, p. 395, Oct. 12, 1987.

Seedorf, Chem. Abstr., vol. 106:132597s, p. 152, Apr. 27, 1987.

Li, Medline File 154, No. 06310140, 1987.

Krisch, Medline File 83, No. 85005364, 1984.

*Primary Examiner*—Mary E. Mosher
*Assistant Examiner*—Donna C. Wortman
*Attorney, Agent, or Firm*—Jacobson, Price, Holman & Stern, PLLC

[57] ABSTRACT

Method for detection of infection with human papillomavirus (HPV) for diagnostic purposes, particularly for diagnosing carcinoma, or pre-stages thereof, or the risk of development of carcinoma. The detection is effected on a body fluid, particularly on a secretion from cervix uteri, by ascertaining the presence of IgA, IgG and IgM antibodies against papillomavirus virions, including individual virion proteins or peptides thereof, in the body fluid.

41 Claims, 16 Drawing Sheets

Figure 12:
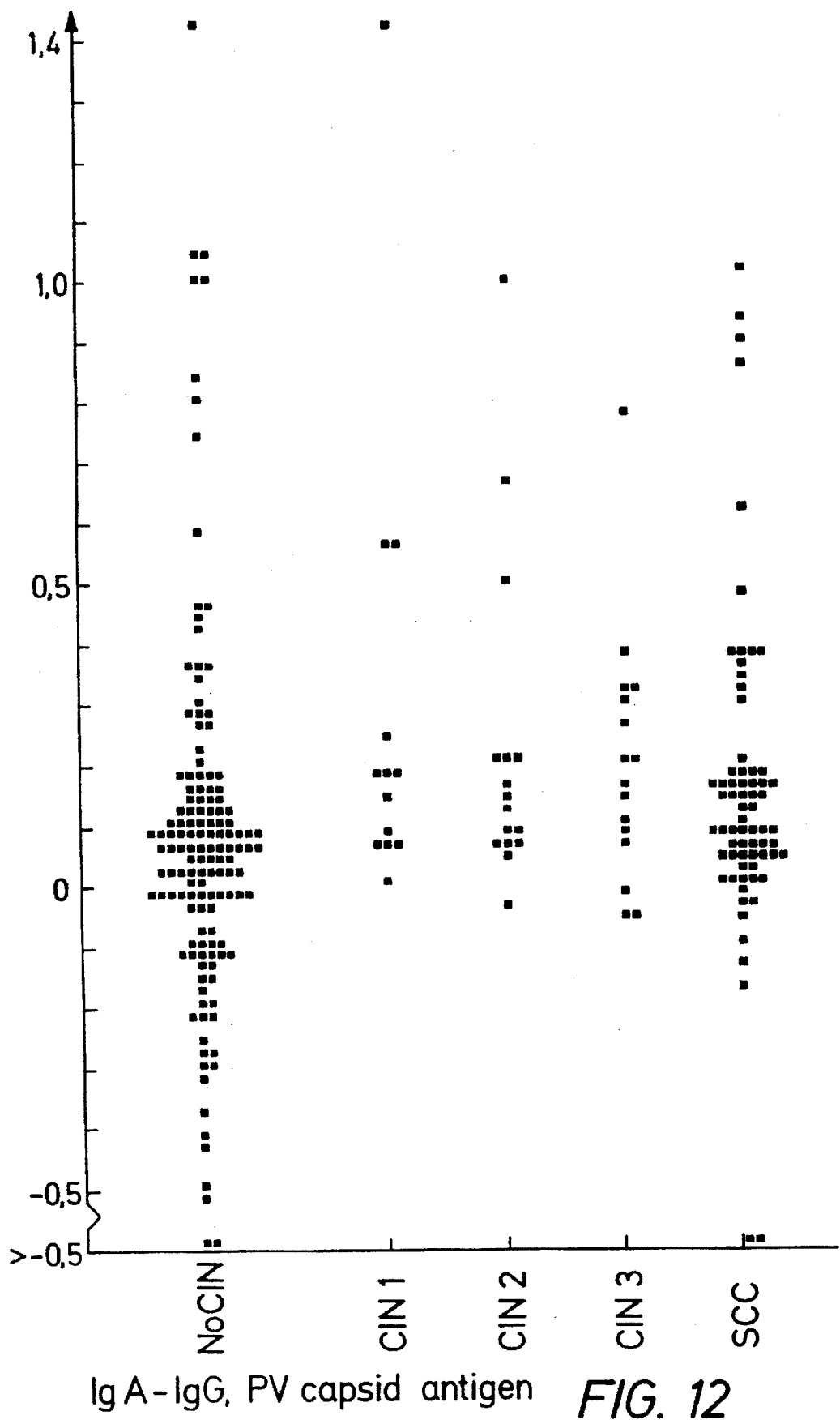

IgA-IgG, PV capsid antigen  FIG. 12

SEQUENCE LISTING ( 1 ) GENERAL INFORMATION:

( i i i ) NUMBER OF SEQUENCES: 67

( 2 ) INFORMATION FOR SEQ ID NO: 1:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 1:

```
Gln  Val  Thr  Phe  Ile  Tyr  Ile  Leu  Val  Ile
1                   5                        10

Thr  Cys  Tyr  Glu  Asn  Asp  Val  Asn  Val  Tyr
                    15                       20
```

( 2 ) INFORMATION FOR SEQ ID NO: 2:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 2:

```
Asp  Val  Asn  Val  Tyr  His  Ile  Phe  Phe  Gln
1                   5                        10

Met  Ser  Leu  Trp  Leu  Pro  Ser  Glu  Ala  Thr
                    15                       20
```

( 2 ) INFORMATION FOR SEQ ID NO: 3:

( i ) SEQUENCE CHARACTERISTICS:
        ( A ) LENGTH: 20 amio acids
        ( B ) TYPE: amino acid
        ( C ) TOPOLOGY: linear ( x i ) SEQUENCE DESCRIPTION: SEQ ID NO: 3:

```
Pro  Ser  Glu  Ala  Thr  Val  Tyr  Leu  Pro  Pro
```

```
1                    5                       10

Val  Pro  Val  Ser  Lys  Val  Val  Ser  Thr  Asp
                    15                      20
```

(2) INFORMATION FOR SEQ ID NO: 4:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 4:

```
Val  Val  Ser  Thr  Asp  Glu  Tyr  Val  Ala  Arg
1                    5                       10

Thr  Asn  Ile  Tyr  Tyr  His  Ala  Gly  Thr  Ser
                    15                      20
```

(2) INFORMATION FOR SEQ ID NO: 5:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 5:

```
His  Ala  Gly  Thr  Ser  Arg  Leu  Leu  Ala  Val
1                    5                       10

Gly  His  Pro  Tyr  Phe  Pro  Ile  Lys  Lys  Pro
                    15                      20
```

(2) INFORMATION FOR SEQ ID NO: 6:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 6:

```
Pro  Ile  Lys  Lys  Pro  Asn  Asn  Asn  Lys  Ile
1                    5                       10

Leu  Val  Pro  Lys  Val  Ser  Gly  Leu  Gln  Tyr
                    15                      20
```

(2) INFORMATION FOR SEQ ID NO: 7:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 7:

```
Ser  Gly  Leu  Gln  Tyr  Arg  Val  Phe  Arg  Ile
1                    5                       10

His  Leu  Pro  Asp  Pro  Asn  Lys  Phe  Gly  Phe
                    15                      20
```

(2) INFORMATION FOR SEQ ID NO: 8:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 8:

```
Asn  Lys  Phe  Gly  Phe  Pro  Asp  Thr  Ser  Phe
```

```
                    1                      5                              10
            Tyr  Asn  Pro  Asp  Thr  Gln  Arg  Leu  Val  Trp
                                      15                        20
```

(2) INFORMATION FOR SEQ ID NO: 9:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 9:

```
Gln  Arg  Leu  Val  Trp  Ala  Cys  Val  Gly  Val
1                   5                        10
Glu  Val  Gly  Arg  Gly  Gln  Pro  Leu  Gly  Val
                    15                       20
```

(2) INFORMATION FOR SEQ ID NO: 10:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 10:

```
Gln  Pro  Leu  Gly  Val  Gly  Ile  Ser  Gly  His
1                   5                        10
Pro  Leu  Leu  Asn  Lys  Leu  Asp  Asp  Thr  Glu
                    15                       20
```

(2) INFORMATION FOR SEQ ID NO: 11:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 11:

```
Leu  Asp  Asp  Thr  Glu  Asn  Ala  Ser  Ala  Tyr
1                   5                        10
Ala  Ala  Asn  Ala  Gly  Val  Asp  Asn  Arg  Glu
                    15                       20
```

(2) INFORMATION FOR SEQ ID NO: 12:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 12:

```
Val  Asp  Asn  Arg  Glu  Cys  Ile  Ser  Met  Asp
1                   5                        10
Tyr  Lys  Gln  Thr  Gln  Leu  Cys  Leu  Ile  Gly
                    15                       20
```

(2) INFORMATION FOR SEQ ID NO: 13:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 13:

```
Leu  Cys  Leu  Ile  Gly  Cys  Lys  Pro  Pro  Ile
```

```
            1               5                          10
Gly  Glu  His  Trp  Gly  Lys  Gly  Ser  Pro  Cys
                         15                          20
```

( 2 ) INFORMATION FOR SEQ ID NO: 14:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 14:

```
Lys  Gly  Ser  Pro  Cys  Thr  Asn  Val  Ala  Val
1                    5                          10
Asn  Pro  Gly  Asp  Cys  Pro  Pro  Leu  Glu  Leu
                    15                          20
```

( 2 ) INFORMATION FOR SEQ ID NO: 15:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 15:

```
Pro  Pro  Leu  Glu  Leu  Ile  Asn  Thr  Val  Ile
1                    5                          10
Gln  Asp  Gly  Asp  Met  Val  His  Thr  Gly  Phe
                    15                          20
```

( 2 ) INFORMATION FOR SEQ ID NO: 16:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 16:

```
Val  His  Thr  Gly  Phe  Gly  Ala  Met  Asp  Phe
1                    5                          10
Thr  Thr  Leu  Gln  Ala  Asn  Lys  Ser  Glu  Val
                    15                          20
```

( 2 ) INFORMATION FOR SEQ ID NO: 17:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 17:

```
Asn  Lys  Ser  Glu  Val  Pro  Leu  Asp  Ile  Cys
1                    5                          10
Thr  Ser  Ile  Cys  Lys  Tyr  Pro  Asp  Tyr  Ile
                    15                          20
```

( 2 ) INFORMATION FOR SEQ ID NO: 18:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 18:

```
Tyr  Pro  Asp  Tyr  Ile  Lys  Met  Val  Ser  Glu
```

```
                    1               5                              10
Pro  Tyr  Gly  Asp  Ser  Leu  Phe  Phe  Tyr  Leu
                              15                              20
```

( 2 ) INFORMATION FOR SEQ ID NO: 19:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 19:

```
Leu  Phe  Phe  Tyr  Leu  Arg  Arg  Glu  Gln  Met
1                    5                              10
Phe  Val  Arg  His  Leu  Phe  Asn  Arg  Ala  Gly
                              15                              20
```

( 2 ) INFORMATION FOR SEQ ID NO: 20:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 20:

```
Phe  Asn  Arg  Ala  Gly  Thr  Val  Gly  Glu  Asn
1                    5                              10
Val  Pro  Asp  Asp  Leu  Tyr  Ile  Lys  Gly  Ser
                              15                              20
```

( 2 ) INFORMATION FOR SEQ ID NO: 21:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 21:

```
Tyr  Ile  Lys  Gly  Ser  Gly  Ser  Thr  Ala  Asn
1                    5                              10
Leu  Ala  Ser  Ser  Asn  Tyr  Phe  Pro  Thr  Pro
                              15                              20
```

( 2 ) INFORMATION FOR SEQ ID NO: 22:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 22:

```
Tyr  Phe  Pro  Thr  Pro  Ser  Gly  Ser  Met  Val
1                    5                              10
Thr  Ser  Asp  Ala  Gln  Ile  Phe  Asn  Lys  Pro
                              15                              20
```

( 2 ) INFORMATION FOR SEQ ID NO: 23:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 23:

```
Ile  Phe  Asn  Lys  Pro  Tyr  Trp  Leu  Gln  Arg
```

```
            1                     5                        10
Ala   Gln   Gly   His   Asn   Asn   Gly   Ile   Cys   Trp
                              15                         20
```

( 2 ) INFORMATION FOR SEQ ID NO: 24:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 24:

```
Asn   Gly   Ile   Cys   Trp   Gly   Asn   Gln   Leu   Phe
 1                      5                               10

Val   Thr   Val   Val   Asp   Thr   Thr   Arg   Ser   Thr
                        15                              20
```

( 2 ) INFORMATION FOR SEQ ID NO: 25:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 25:

```
Thr   Thr   Arg   Ser   Thr   Asn   Met   Ser   Leu   Cys
 1                      5                               10

Ala   Ala   Ile   Ser   Thr   Ser   Glu   Thr   Thr   Tyr
                        15                              20
```

( 2 ) INFORMATION FOR SEQ ID NO: 26:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 26:

```
Ser   Glu   Thr   Thr   Tyr   Lys   Asn   Thr   Asn   Phe
 1                      5                               10

Lys   Glu   Tyr   Leu   Arg   His   Gly   Glu   Glu   Tyr
                        15                              20
```

( 2 ) INFORMATION FOR SEQ ID NO: 27:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 27:

```
His   Gly   Glu   Glu   Tyr   Asp   Leu   Gln   Phe   Ile
 1                      5                               10

Phe   Gln   Leu   Cys   Lys   Ile   Thr   Leu   Thr   Ala
                        15                              20
```

( 2 ) INFORMATION FOR SEQ ID NO: 28:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 28:

```
Ile   Thr   Leu   Thr   Ala   Asp   Val   Met   Thr   Tyr
```

```
1                 5                          1 0
Ile  His  Ser  Met  Asn  Ser  Thr  Ile  Leu  Glu
                     1 5                     2 0
```

( 2 ) INFORMATION FOR SEQ ID NO: 29:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 29:

```
Ser  Thr  Ile  Leu  Glu  Asp  Trp  Asn  Phe  Gly
1                 5                          1 0
Leu  Gln  Pro  Pro  Pro  Gly  Gly  Thr  Leu  Glu
                     1 5                     2 0
```

( 2 ) INFORMATION FOR SEQ ID NO: 30:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 30:

```
Gly  Gly  Thr  Leu  Glu  Asp  Thr  Tyr  Arg  Phe
1                 5                          1 0
Val  Thr  Gln  Ala  Ile  Ala  Cys  Gln  Lys  His
                     1 5                     2 0
```

( 2 ) INFORMATION FOR SEQ ID NO: 31:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 31:

```
Ala  Cys  Gln  Lys  His  Thr  Pro  Pro  Ala  Pro
1                 5                          1 0
Lys  Glu  Asp  Asp  Pro  Leu  Lys  Lys  Tyr  Thr
                     1 5                     2 0
```

( 2 ) INFORMATION FOR SEQ ID NO: 32:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 32:

```
Leu  Lys  Lys  Tyr  Thr  Phe  Trp  Glu  Val  Asn
1                 5                          1 0
Leu  Lys  Glu  Lys  Phe  Ser  Ala  Asp  Leu  Asp
                     1 5                     2 0
```

( 2 ) INFORMATION FOR SEQ ID NO: 33:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 33:

```
Ser  Ala  Asp  Leu  Asp  Gln  Phe  Pro  Leu  Gly
```

```
               1               5                              10
Arg  Lys  Phe  Leu  Leu  Gln  Ala  Gly  Leu  Lys
                              15                              20
```

( 2 ) INFORMATION FOR SEQ ID NO: 34:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 34:

```
Gln  Ala  Gly  Leu  Lys  Ala  Lys  Pro  Lys  Phe
1                   5                         10
Thr  Leu  Gly  Lys  Arg  Lys  Ala  Thr  Pro  Thr
                   15                         20
```

( 2 ) INFORMATION FOR SEQ ID NO: 35:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 35:

```
Lys  Ala  Thr  Pro  Thr  Thr  Ser  Ser  Thr  Ser
1                   5                         10
Thr  Thr  Ala  Lys  Arg  Lys  Lys  Arg  Lys  Leu
                   15                         20
```

( 2 ) INFORMATION FOR SEQ ID NO: 36:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 36:

```
Arg  His  Lys  Arg  Ser  Ala  Lys  Arg  Thr  Lys
1                   5                         10
Arg  Ala  Ser  Ala  Thr  Gln  Leu  Tyr  Lys  Thr
                   15                         20
```

( 2 ) INFORMATION FOR SEQ ID NO: 37:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 37:

```
Gln  Leu  Tyr  Lys  Thr  Cys  Lys  Gln  Ala  Gly
1                   5                         10
Thr  Cys  Pro  Pro  Asp  Ile  Ile  Pro  Lys  Val
                   15                         20
```

( 2 ) INFORMATION FOR SEQ ID NO: 38:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 38:

```
Ile  Ile  Pro  Lys  Val  Glu  Gly  Lys  Thr  Ile
```

```
1               5                       10
Ala  Glu  Gln  Ile  Leu  Gln  Tyr  Gly  Ser  Met
                         15                      20
```

(2) INFORMATION FOR SEQ ID NO: 39:

(i) SEQUENCE CHARACTERISTICS:
        (A) LENGTH: 20 amino acids
        (B) TYPE: amino acid
        (C) TOPOLOGY: linear (x i) SEQUENCE DESCRIPTION: SEQ ID NO: 39:

```
Gln  Tyr  Gly  Ser  Met  Gly  Val  Phe  Phe  Gly
1                   5                        10
Gly  Leu  Gly  Ile  Gly  Thr  Gly  Ser  Gly  Thr
                         15                      20
```

(2) INFORMATION FOR SEQ ID NO: 40:

(i) SEQUENCE CHARACTERISTICS:
        (A) LENGTH: 20 amino acids
        (B) TYPE: amino acid
        (C) TOPOLOGY: linear (x i) SEQUENCE DESCRIPTION: SEQ ID NO: 40:

```
Thr  Gly  Ser  Gly  Thr  Gly  Gly  Arg  Thr  Gly
1                   5                        10
Tyr  Ile  Pro  Leu  Gly  Thr  Arg  Pro  Pro  Thr
                         15                      20
```

(2) INFORMATION FOR SEQ ID NO: 41:

(i) SEQUENCE CHARACTERISTICS:
        (A) LENGTH: 20 amino acids
        (B) TYPE: amino acid
        (C) TOPOLOGY: linear (x i) SEQUENCE DESCRIPTION: SEQ ID NO: 41:

```
Thr  Arg  Pro  Pro  Thr  Ala  Thr  Asp  Thr  Leu
1                   5                        10
Ala  Pro  Val  Arg  Pro  Pro  Leu  Thr  Val  Asp
                         15                      20
```

(2) INFORMATION FOR SEQ ID NO: 42:

(i) SEQUENCE CHARACTERISTICS:
        (A) LENGTH: 20 amino acids
        (B) TYPE: amino acid
        (C) TOPOLOGY: linear (x i) SEQUENCE DESCRIPTION: SEQ ID NO: 42:

```
Pro  Leu  Thr  Val  Asp  Pro  Val  Gly  Pro  Ser
1                   5                        10
Asp  Pro  Ser  Ile  Val  Ser  Leu  Val  Glu  Glu
                         15                      20
```

(2) INFORMATION FOR SEQ ID NO: 43:

(i) SEQUENCE CHARACTERISTICS:
        (A) LENGTH: 20 amino acids
        (B) TYPE: amino acid
        (C) TOPOLOGY: linear (x i) SEQUENCE DESCRIPTION: SEQ ID NO: 43:

```
Ser  Leu  Val  Glu  Glu  Thr  Ser  Phe  Ile  Asp
```

```
           1               5                          10
Ala  Gly  Ala  Pro  Thr  Ser  Val  Pro  Ser  Ile
                        15                          20
```

(2) INFORMATION FOR SEQ ID NO: 44:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 44:

```
Ser  Val  Pro  Ser  Ile  Pro  Pro  Asp  Val  Ser
1                   5                          10
Gly  Phe  Ser  Ile  Thr  Thr  Ser  Thr  Asp  Thr
                        15                          20
```

(2) INFORMATION FOR SEQ ID NO: 45:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 45:

```
Thr  Ser  Thr  Asp  Thr  Thr  Pro  Ala  Ile  Leu
1                   5                          10
Asp  Ile  Asn  Asn  Thr  Val  Thr  Thr  Val  Thr
                        15                          20
```

(2) INFORMATION FOR SEQ ID NO: 46:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 46:

```
Val  Thr  Thr  Val  Thr  Thr  His  Asn  Asn  Pro
1                   5                          10
Thr  Phe  Thr  Asp  Pro  Ser  Val  Leu  Gln  Pro
                        15                          20
```

(2) INFORMATION FOR SEQ ID NO: 47:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 47:

```
Ser  Val  Leu  Gln  Pro  Pro  Thr  Pro  Ala  Glu
1                   5                          10
Thr  Gly  Gly  His  Phe  Thr  Leu  Ser  Ser  Ser
                        15                          20
```

(2) INFORMATION FOR SEQ ID NO: 48:

(i) SEQUENCE CHARACTERISTICS:
        (A) LENGTH: 20 amino acids
        (B) TYPE: amino acid
        (C) TOPOLOGY: linear (xi) SEQUENCE DESCRIPTION: SEQ ID NO: 48:

```
Thr  Leu  Ser  Ser  Ser  Thr  Ile  Ser  Thr  His
```

```
1                   5                       10
Asn  Tyr  Glu  Glu  Ile  Pro  Met  Asp  Thr  Phe
                         15                      20
```

( 2 ) INFORMATION FOR SEQ ID NO: 49:

( i ) SEQUENCE CHARACTERISTICS:
      ( A ) LENGTH: 20 amino acids
      ( B ) TYPE: amino acid
      ( C ) TOPOLOGY: linear ( x i ) SEQUENCE DESCRIPTION: SEQ ID NO: 49:

```
Pro  Met  Asp  Thr  Phe  Ile  Val  Ser  Thr  Asn
1                   5                       10
Pro  Asn  Thr  Val  Thr  Ser  Ser  Thr  Pro  Ile
                         15                      20
```

( 2 ) INFORMATION FOR SEQ ID NO: 50:

( i ) SEQUENCE CHARACTERISTICS:
      ( A ) LENGTH: 20 amino acids
      ( B ) TYPE: amino acid
      ( C ) TOPOLOGY: linear ( x i ) SEQUENCE DESCRIPTION: SEQ ID NO: 50:

```
Ser  Ser  Thr  Pro  Ile  Pro  Gly  Ser  Arg  Pro
1                   5                       10
Val  Ala  Arg  Leu  Gly  Leu  Tyr  Ser  Arg  Thr
                         15                      20
```

( 2 ) INFORMATION FOR SEQ ID NO: 51:

( i ) SEQUENCE CHARACTERISTICS:
      ( A ) LENGTH: 20 amino acids
      ( B ) TYPE: amino acid
      ( C ) TOPOLOGY: linear ( x i ) SEQUENCE DESCRIPTION: SEQ ID NO: 51:

```
Leu  Tyr  Ser  Arg  Thr  Thr  Gln  Gln  Val  Lys
1                   5                       10
Val  Val  Asp  Pro  Ala  Phe  Val  Thr  Thr  Pro
                         15                      20
```

( 2 ) INFORMATION FOR SEQ ID NO: 52:

( i ) SEQUENCE CHARACTERISTICS:
      ( A ) LENGTH: 20 amino acids
      ( B ) TYPE: amino acid
      ( C ) TOPOLOGY: linear ( x i ) SEQUENCE DESCRIPTION: SEQ ID NO: 52:

```
Phe  Val  Thr  Thr  Pro  Thr  Lys  Leu  Ile  Thr
1                   5                       10
Tyr  Asp  Asn  Pro  Ala  Tyr  Glu  Gly  Ile  Asp
                         15                      20
```

( 2 ) INFORMATION FOR SEQ ID NO: 53:

( i ) SEQUENCE CHARACTERISTICS:
      ( A ) LENGTH: 20 amino acids
      ( B ) TYPE: amino acid
      ( C ) TOPOLOGY: linear ( x i ) SEQUENCE DESCRIPTION: SEQ ID NO: 53:

```
Tyr  Glu  Gly  Ile  Asp  Val  Asp  Asn  Thr  Leu
```

```
1                   5                        10
Tyr  Phe  Ser  Ser  Asn  Asp  Asn  Ser  Ile  Asn
                    15                       20
```

( 2 ) INFORMATION FOR SEQ ID NO: 54:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 54:

```
Asp  Asn  Ser  Ile  Asn  Ile  Ala  Pro  Asp  Pro
1                   5                        10
Asp  Phe  Leu  Asp  Ile  Val  Ala  Leu  His  Arg
                    15                       20
```

( 2 ) INFORMATION FOR SEQ ID NO: 55:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 55:

```
Val  Ala  Leu  His  Arg  Pro  Ala  Leu  Thr  Ser
1                   5                        10
Arg  Arg  Thr  Gly  Ile  Arg  Tyr  Ser  Arg  Ile
                    15                       20
```

( 2 ) INFORMATION FOR SEQ ID NO: 56:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 56:

```
Arg  Tyr  Ser  Arg  Ile  Gly  Asn  Lys  Gln  Thr
1                   5                        10
Leu  Arg  Thr  Arg  Ser  Gly  Lys  Ser  Ile  Gly
                    15                       20
```

( 2 ) INFORMATION FOR SEQ ID NO: 57:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 57:

```
Gly  Lys  Ser  Ile  Gly  Ala  Lys  Val  His  Tyr
1                   5                        10
Tyr  Tyr  Asp  Leu  Ser  Thr  Ile  Asp  Pro  Ala
                    15                       20
```

( 2 ) INFORMATION FOR SEQ ID NO: 58:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 58:

```
Thr  Ile  Asp  Pro  Ala  Glu  Glu  Ile  Glu  Leu
```

```
             1               5                              10
Gln  Thr  Ile  Thr  Pro  Ser  Thr  Tyr  Thr  Thr
                              15                            20
```

( 2 ) INFORMATION FOR SEQ ID NO: 59:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 59:

```
Ser  Thr  Tyr  Thr  Thr  Thr  Ser  His  Ala  Ala
 1                       5                            10

Ser  Pro  Thr  Ser  Ile  Asn  Asn  Gly  Leu  Tyr
                         15                           20
```

( 2 ) INFORMATION FOR SEQ ID NO: 60:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 60:

```
Asn  Asn  Gly  Leu  Tyr  Asp  Ile  Tyr  Ala  Asp
 1                       5                            10

Asp  Phe  Ile  Thr  Asp  Thr  Ser  Thr  Thr  Pro
                         15                           20
```

( 2 ) INFORMATION FOR SEQ ID NO: 61:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 61:

```
Thr  Ser  Thr  Thr  Pro  Val  Pro  Ser  Val  Pro
 1                       5                            10

Ser  Thr  Ser  Leu  Ser  Gly  Tyr  Ile  Pro  Ala
                         15                           20
```

( 2 ) INFORMATION FOR SEQ ID NO: 62:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 62:

```
Gly  Tyr  Ile  Pro  Ala  Asn  Thr  Thr  Ile  Pro
 1                       5                            10

Phe  Gly  Gly  Ala  Tyr  Asn  Ile  Pro  Leu  Val
                         15                           20
```

( 2 ) INFORMATION FOR SEQ ID NO: 63:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 63:

```
Asn  Ile  Pro  Leu  Val  Ser  Gly  Pro  Asp  Ile
```

-continued

```
         1                    5                              10
Pro   Ile   Asn   Ile   Thr   Asp   Gln   Ala   Pro   Ser
                         15                               20
```

( 2 ) INFORMATION FOR SEQ ID NO: 64:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO: 64:

```
Asp   Gln   Ala   Pro   Ser   Leu   Ile   Pro   Ile   Val
 1                       5                               10
Pro   Gly   Ser   Pro   Gln   Tyr   Thr   Ile   Ile   Ala
                         15                               20
```

( 2 ) INFORMATION FOR SEQ ID NO: 65:

( i ) SEQUENCE CHARACTERISTICS:
        ( A ) LENGTH: 21 amino acids
        ( B ) TYPE: amino acid
        ( C ) TOPOLOGY: linear ( x i ) SEQUENCE DESCRIPTION: SEQ ID NO: 65:

```
Tyr   Thr   Ile   Ile   Ala   Asp   Ala   Gly   Asp   Phe
 1                       5                               10
Tyr   Leu   His   Pro   Ser   Tyr   Tyr   Met   Leu   Arg
                         15                               20
Lys
 21
```

( 2 ) INFORMATION FOR SEQ ID NO: 66:

( i ) SEQUENCE CHARACTERISTICS:
        ( A ) LENGTH: 21 amino acids
        ( B ) TYPE: amino acid
        ( C ) TOPOLOGY: linear ( x i ) SEQUENCE DESCRIPTION: SEQ ID NO: 66:

```
Tyr   Met   Leu   Arg   Lys   Arg   Arg   Lys   Arg   Leu
 1                       5                               10
Pro   Tyr   Phe   Phe   Ser   Asp   Val   Ser   Leu   Ala
                         15                               20
Ala
 21
```

( 2 ) INFORMATION FOR SEQ ID NO: 67:

( i ) SEQUENCE CHARACTERISTICS:
        ( A ) LENGTH: 19 amino acids
        ( B ) TYPE: amino acid
        ( C ) TOPOLOGY: linear ( x i ) SEQUENCE DESCRIPTION: SEQ ID NO: 67:

```
His   Ser   Lys   Ala   Ile   Val   Thr   Leu   Thr   Tyr
 1                       5                               10
Asp   Ser   Glu   Trp   Gln   Arg   Asp   Gln   Cys
                         15
```

METHOD FOR DETECTION OF HUMAN PAPILLOMAVIRUS (HPV) FOR DIAGNOSTIC PURPOSES

The invention relates to a method for detection of infection with human papillomavirus (HPV) for diagnostic purposes.

Human papillomavirus (HPV) infection of the cervix uteri is associated with carcinoma of the cervix uteri. Over 50 different HPV types have been identified. HPV types 6, 11, 16, 18, 31, 33 and 51 have been found to infect the genital tract. Types 6 and 11 cause benign proliferative lesions in the genital tract, condylomata acuminata. Types 16, 18, 31 and 33 are found in pre-cancerous lesions and in a majority of carcinomas of the cervix uteri. The human papillomaviruses are immunologically related to the bovine papillomaviruses: antisera reactive with both groups of viruses can readily be prepared. Papillomavirus capsid antigens have been demonstrated in pre-cancerous lesions and condylomatous tissue using such group-specific antisera prepared against viral capsids. Patients with genital warts, cervical intraepithelial neoplasia (CIN) and carcinoma of the cervix uteri have been reported to have higher serum IgG antibody levels to the group-specific capsid antigen compared to control groups.

The object of the invention is to provide a method of the type referred to above in order to facilitate the detection of carcinoma, particularly cervical carcinoma, or pre-stages thereof, or the risk of development of carcinoma.

Another object of the invention is to provide a method of the type referred to above by means of which the presence of carcinoma, or pre-stages thereof, or the risk of development of carcinoma, can be ascertained in a simple and rapid way by detection of the presence of antibodies to human papillomavirus (HPV) in body fluids.

In order to achieve these and other purposes which will be apparent from the description which follows the method of the invention has obtained the characterising features of claims 1, 11 21 and 31.

Figure 2:
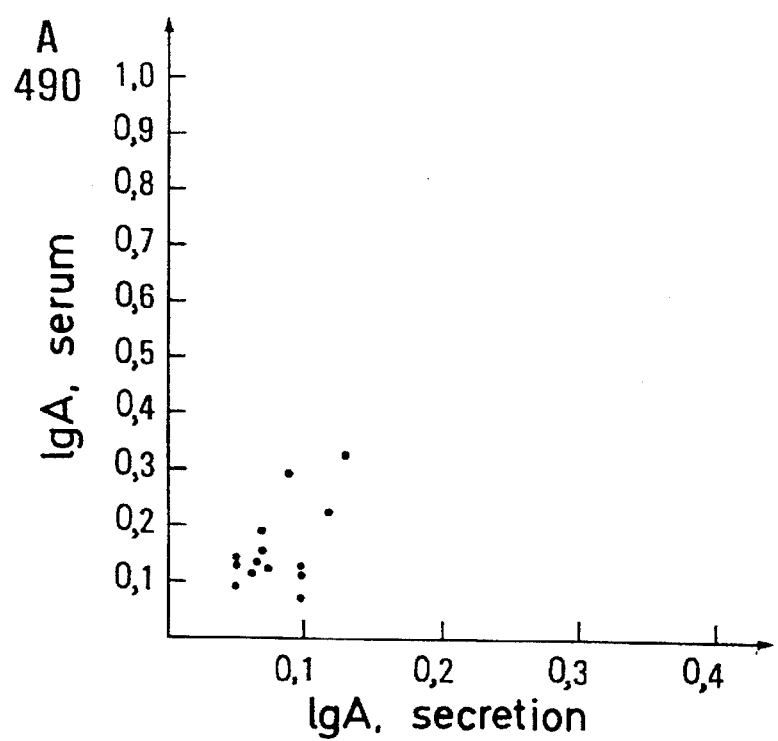
Figure 3:
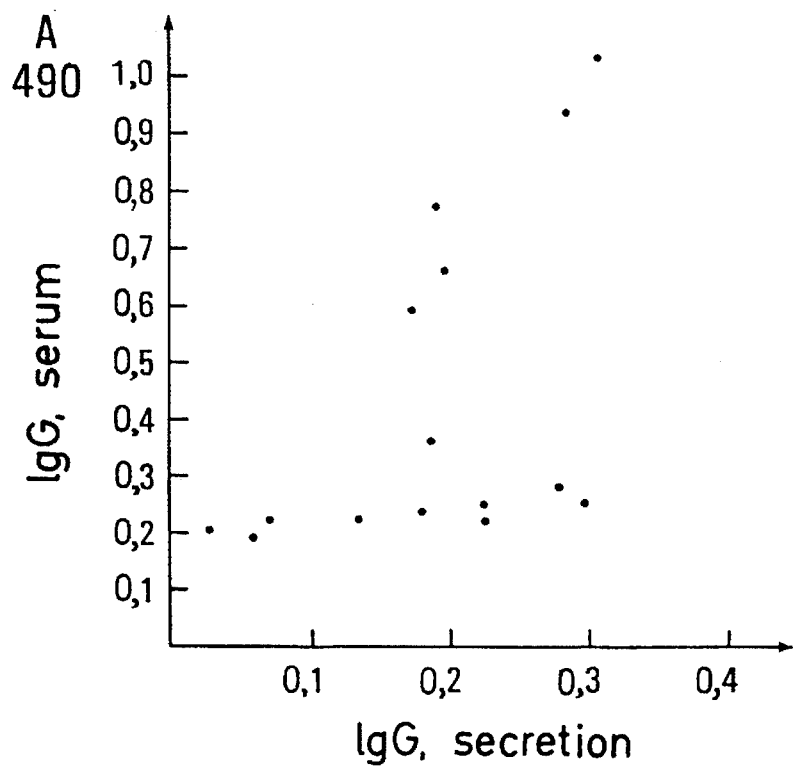
Figure 4:
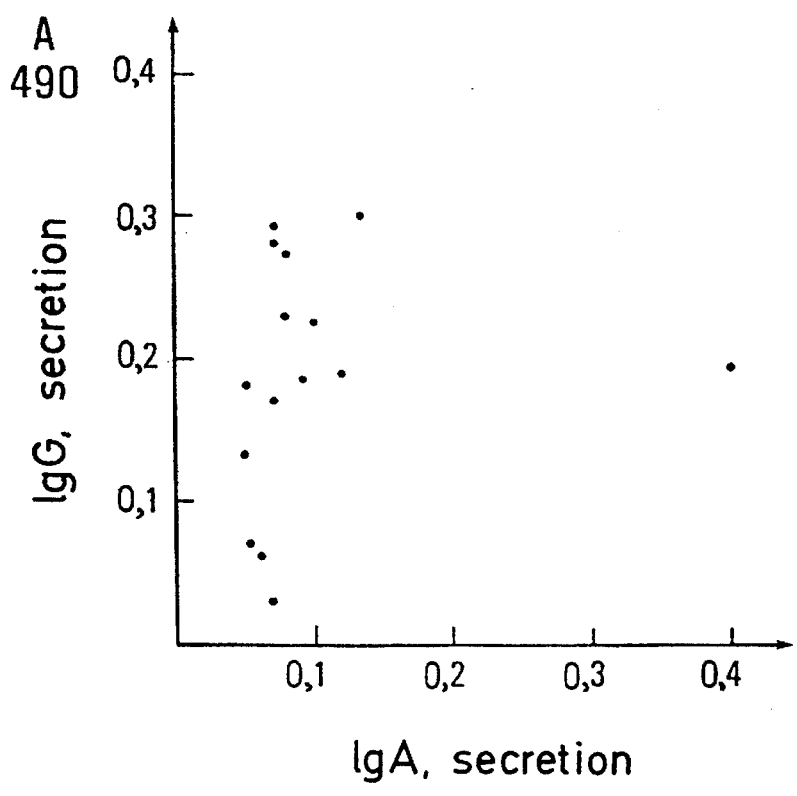
Figure 5:
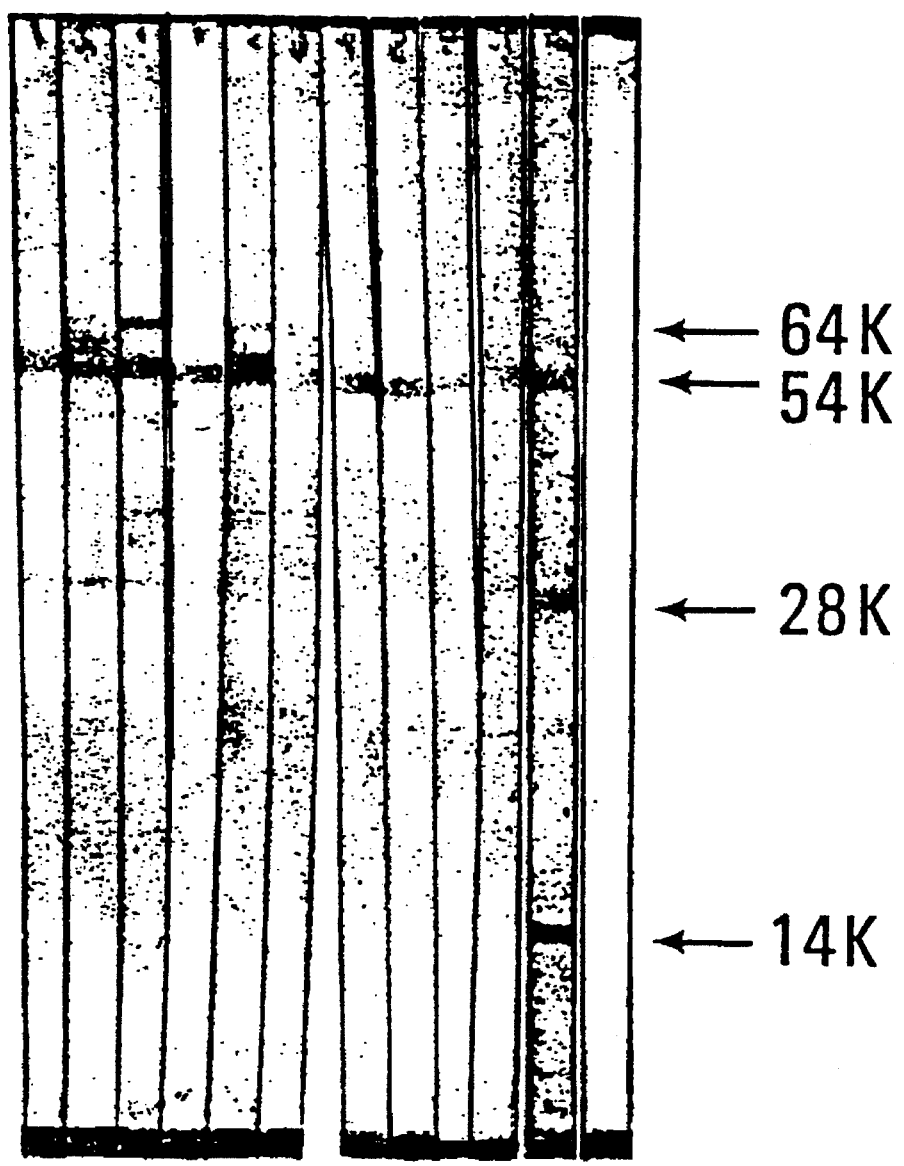
Figure 6:
Figure 7:
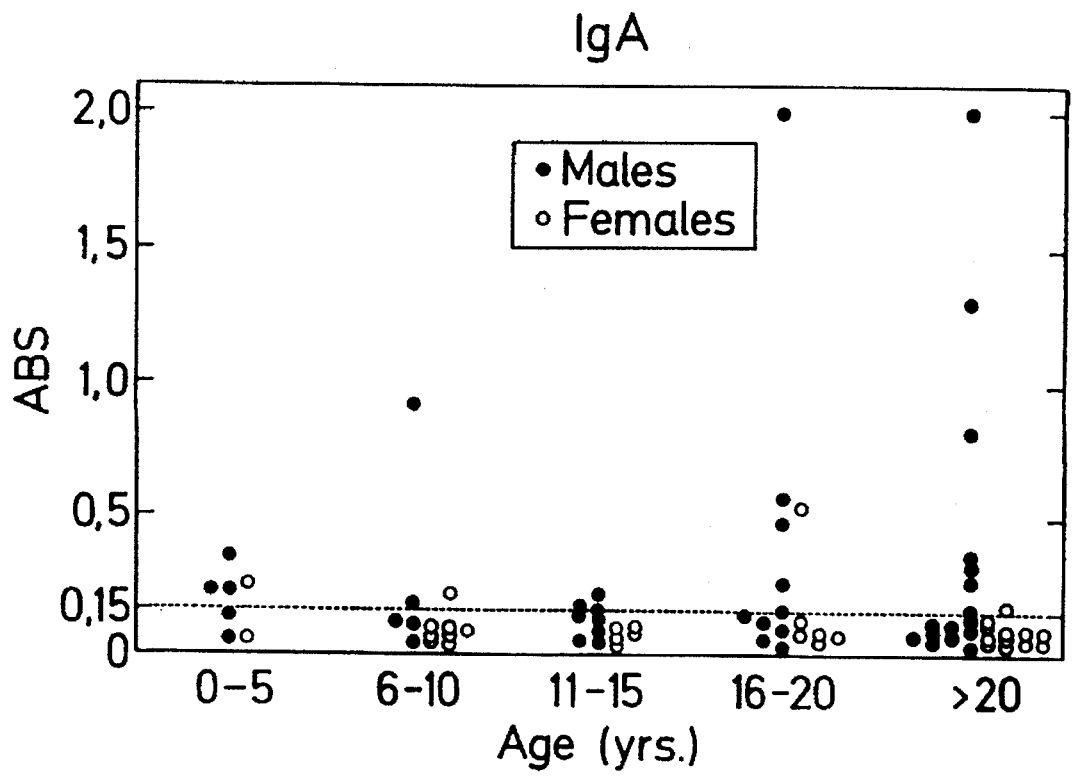
Figure 8:
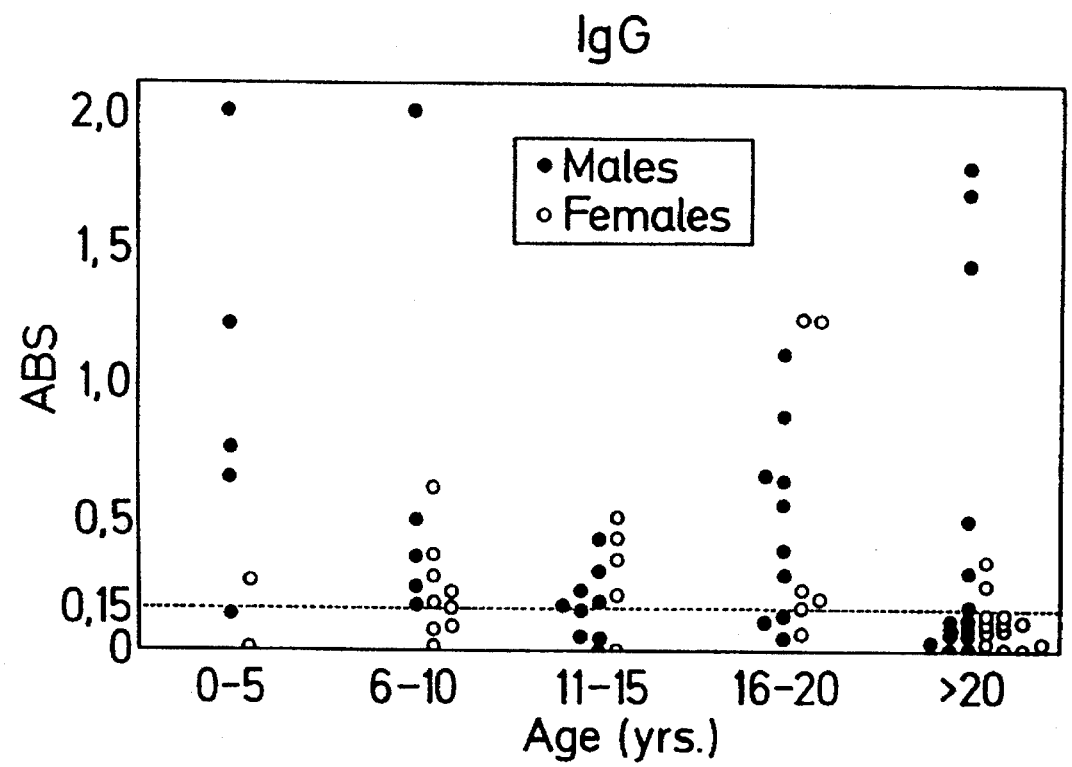
Figure 9:
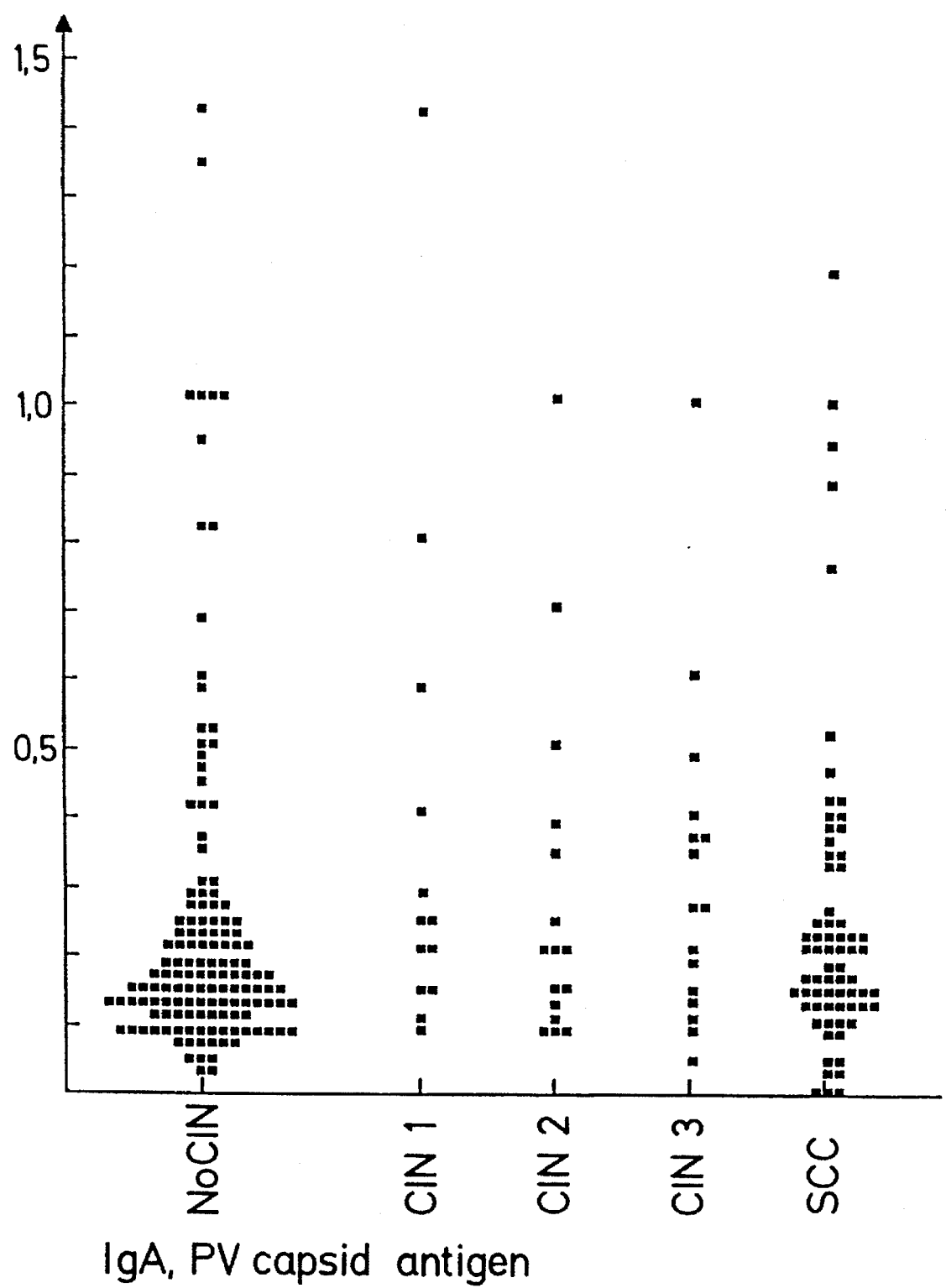
Figure 10:
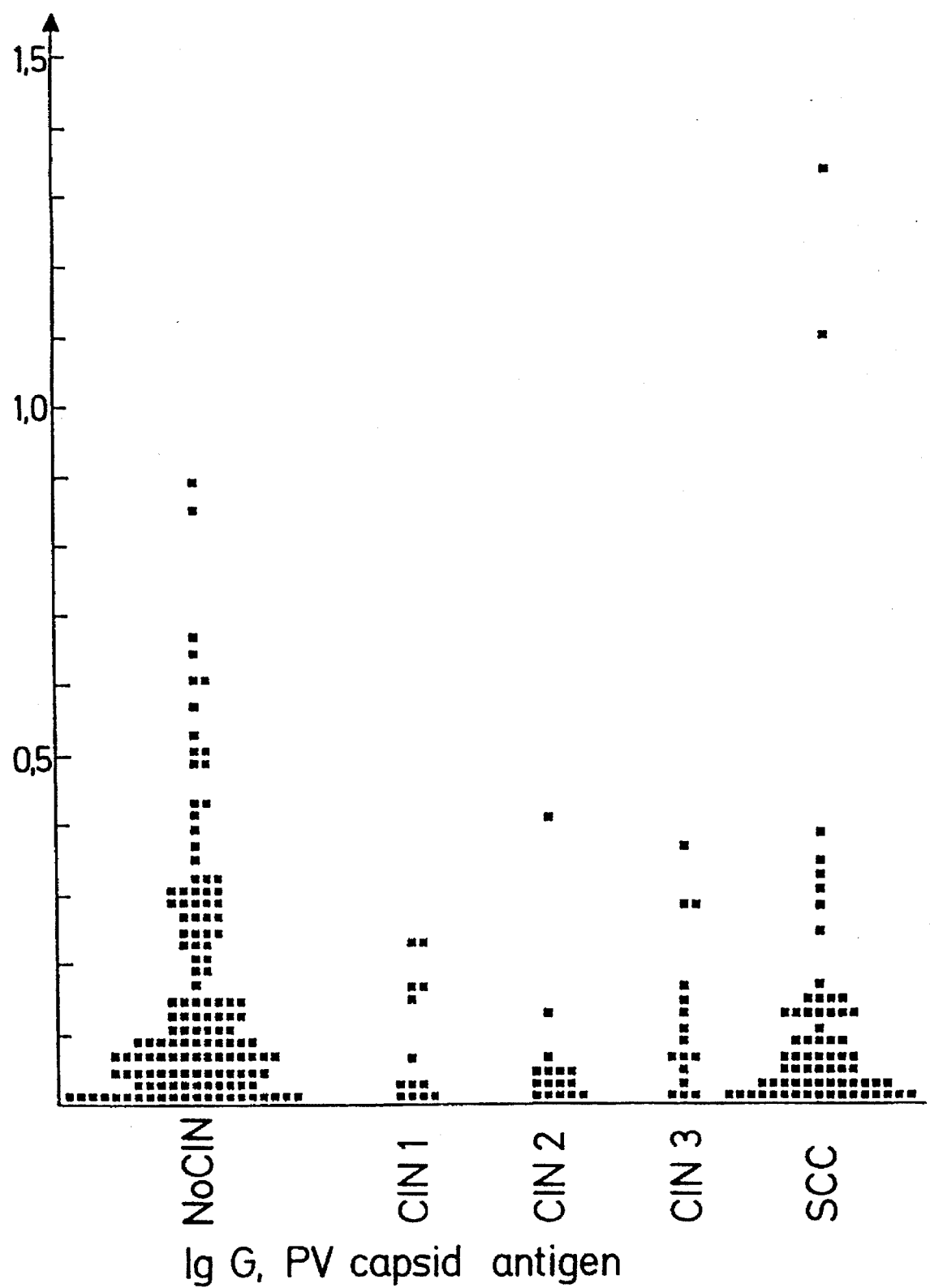
Figure 11:
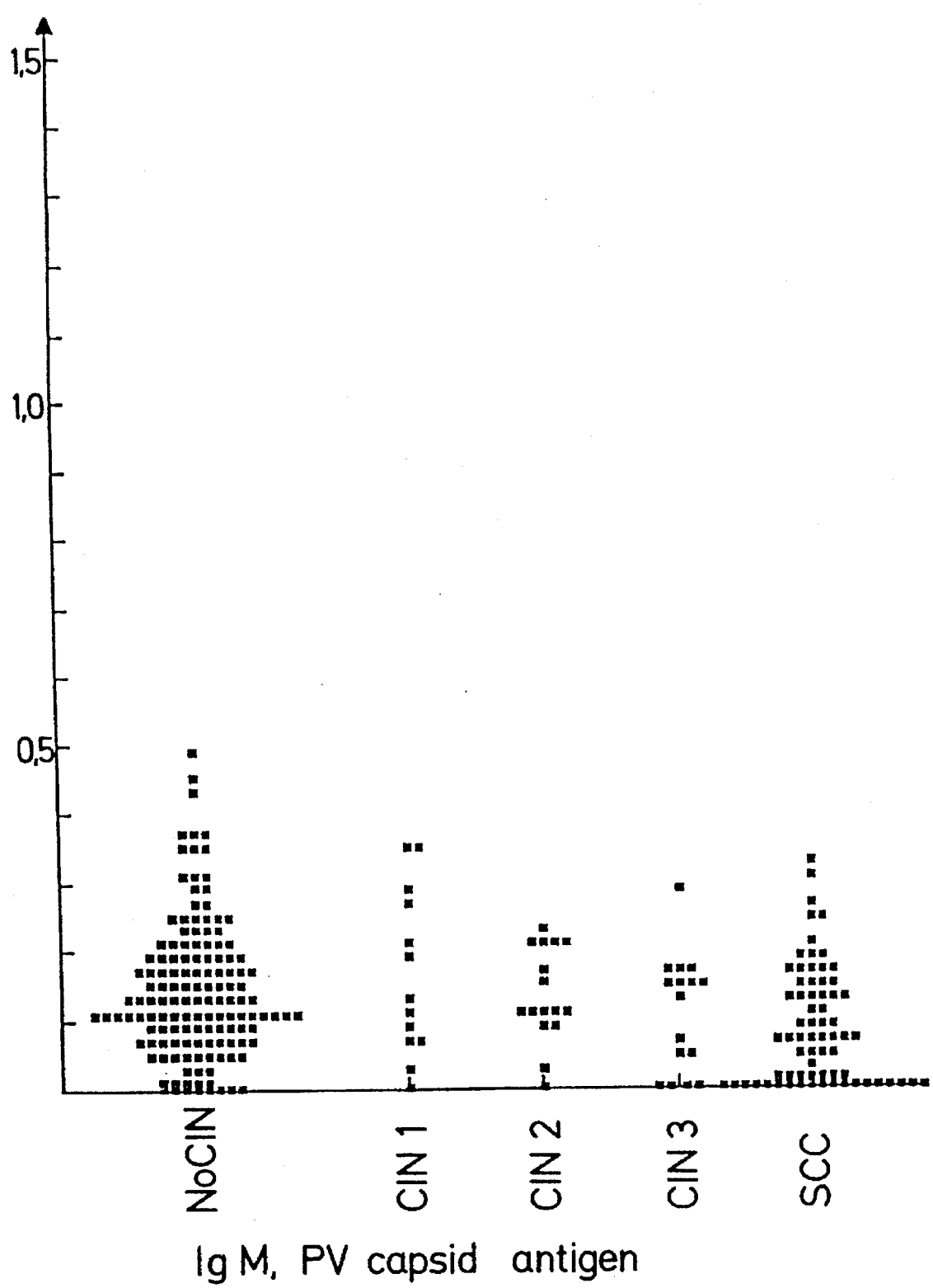
Figure 13:
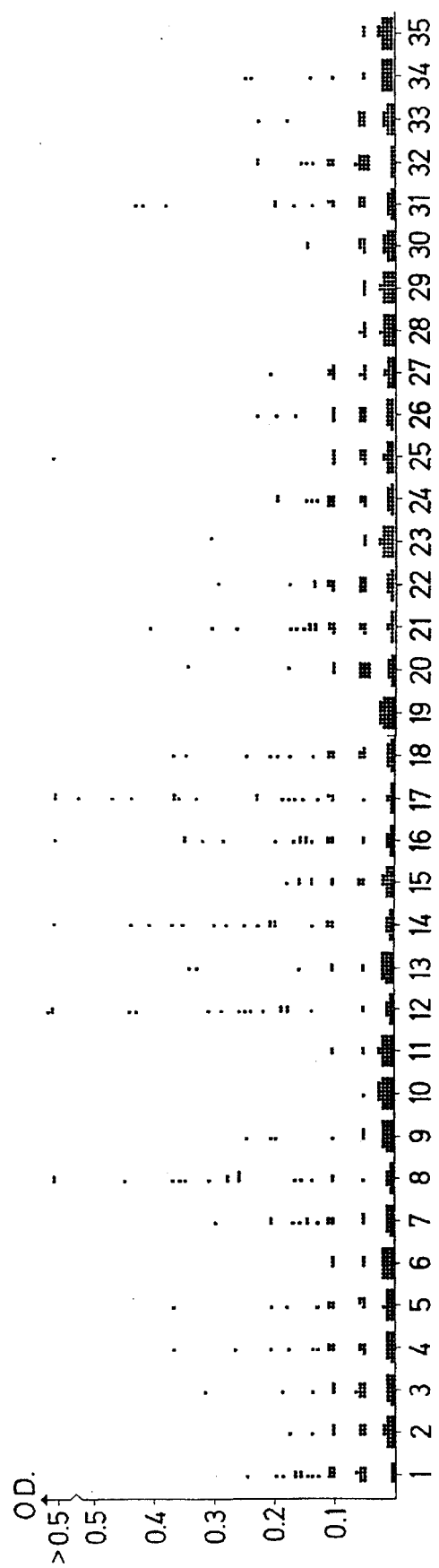
Figure 14:
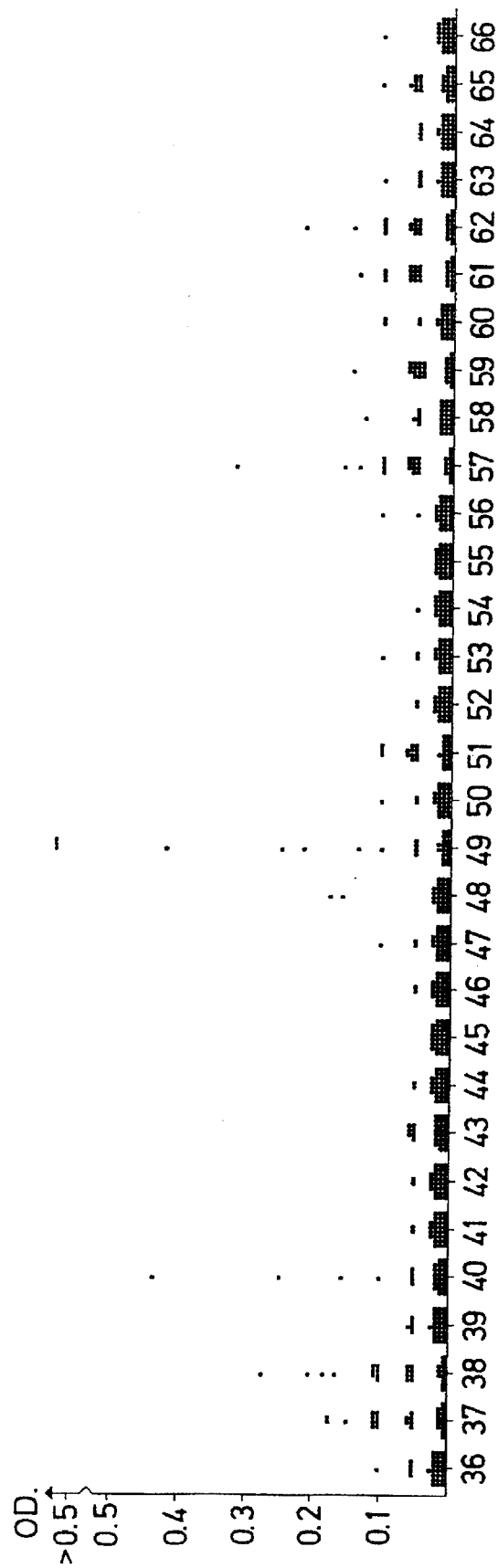
Figure 15:
Figure 16:
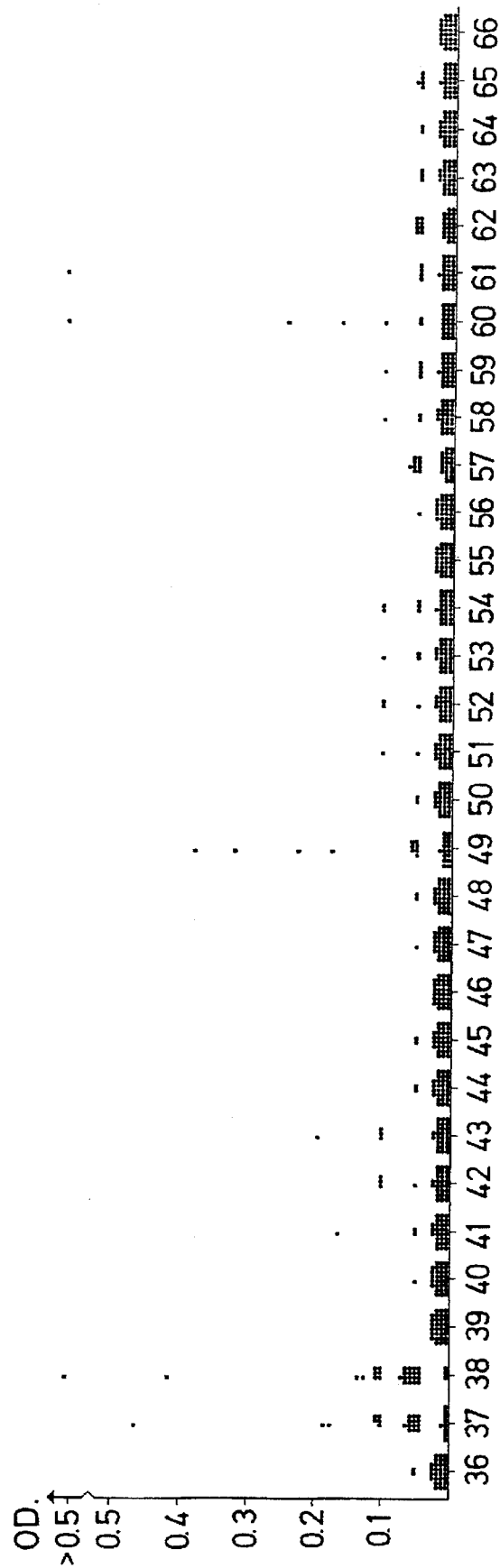
Figure 17:
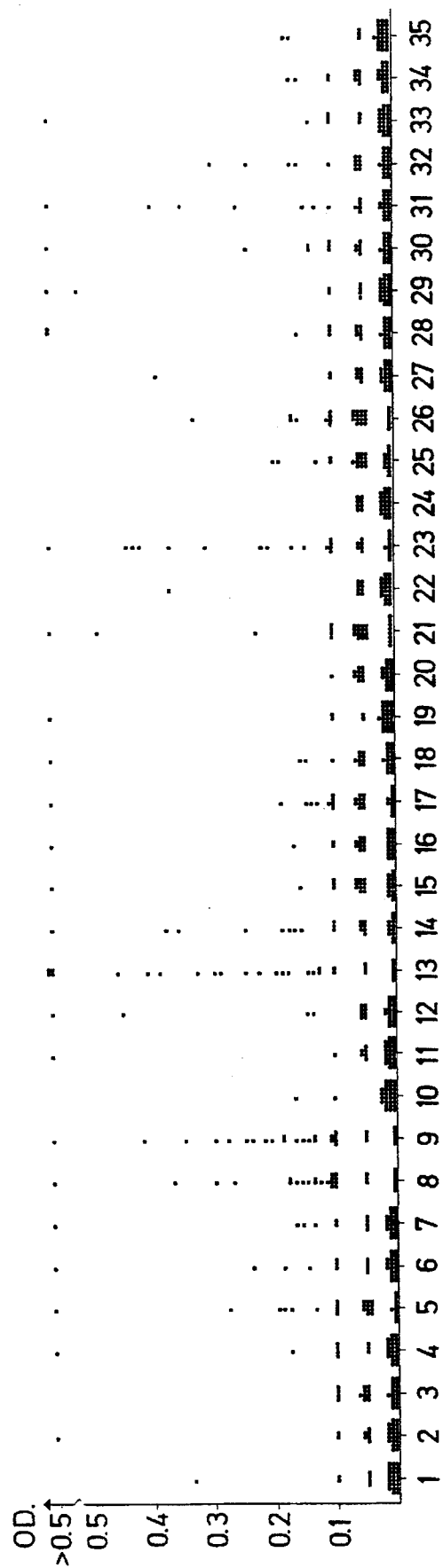
Figure 18:
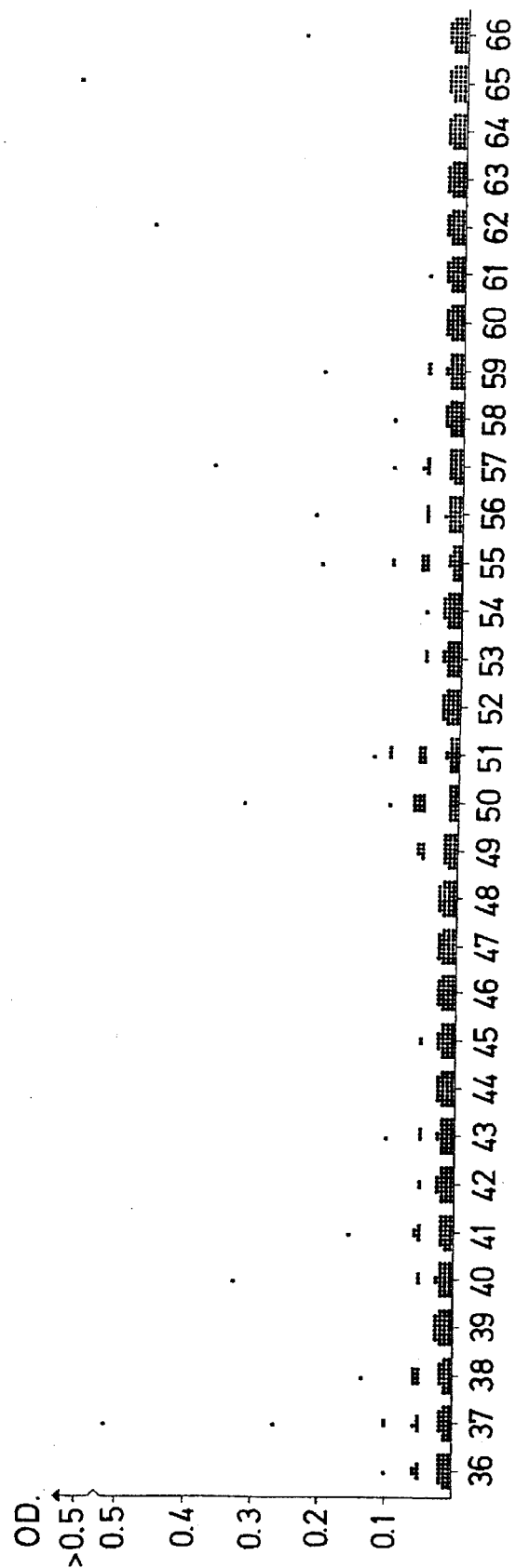
Figure 19:

The invention will be described in more detail below, reference being made to the accompanying drawings in which FIG. 1 is a graph illustrating the detection of IgA antibodies against papillomavirus in cervical secretions, FIG. 2 is a graph illustrating the correlation of IgA antibodies to papillomavirus in serums and cervical secretions, FIG. 3 is a graph illustrating the comparison of IgG antibodies to papillomavirus in serum and vaginal secretions, FIG. 4 is a graph illustrating the comparison of IgA and IgG antibodies against papillomavirus in vaginal secretions, FIG. 5 is a are graph illustrating the detection of IgG antibodies by immunoblotting, FIG. 6 is a graph illustrating the detection of IgA antibodies by immunoblotting, FIG. 7 is a graph illustrating age and sex-related distribution of serum IgA antibodies to PV in a normal population, FIG. 8 is a graph illustrating age and sex-related distribution of serum IgG antibodies to PV in a normal population, FIG. 9 is a graph illustrating detection of IgA antibodies against PV in serum from patients with CIN or carcinoma of the cervix uteri, FIG. 10 is a graph illustrating detection of IgG antibodies to PV in serum from patients with CIN or carcinoma of the cervix uteri, FIG. 11 is a graph illustrating detection of IgM antibodies to PV in serum from patients with CIN or carcinoma of the cervix uteri, FIG. 12 is a graph illustrating the difference between the IgA and IgG response to PV in relation to disease, FIG. 13 is a graph illustrating IgA reactivity to the L1 protein, FIG. 14 is a graph illustrating IgA reactivity to the L2 protein, FIG. 15 is a graph illustrating IgA reactivity to the L1 protein, FIG. 16 is a graph illustrating IgG reactivity to the L2 protein, FIG. 17 is a graph, illustrating IgM reactivity to the L1 protein, FIG. 18 is a graph illustrating IgM reactivity to the L2 protein, and FIG. 19 is a graph illustrating disease-associated reactivity of synthetic peptides.

Table 1 is a graph tabulating comparisons between IgA and IgG antibodies to PV in serum and cervical secretions.

Table 2 is a graph illustrating detection of cervical carcinoma-associated antibodies.

Table 3 is a graph explaining the formula used for synthetic peptides.

Table 4 is a graph illustrating the amino acid sequences of the synthetic peptides.

In order to investigate if IgA antibodies against papillomavirus exist and whether they are correlated with progression to malignancy, cervico-vaginal secretions were examined from patients with condylomata and CIN using a modified ELISA technique.

Forty-two women 20–50 years old participated in the study. They had a previous abnormal vaginal smear and/or condylomas or participated in a screening program. All patients underwent colposcopic examination. A regular Papanicolau smear was taken at the day of colposcopy and in some cases biopsies were taken from colposcopically verified lesions. Cytological and histological examinations were made and matched to ELISA results at the end of the study. Morphologic criteria of HPV infection were made according to Meisels et al (1979). Active papillomavirus infection was suggested by the finding of koilocytotic cells. The typical koilocytotic cell is an intermediate cell with enlarged, hyperchromatic nucleus surrounded by a clear cytoplasmic zone. Cervico-vaginal secretions were collected from endo-ecto cervix and vagina with a small swab. The swab was placed in a glass tube filled with 0.5 ml PBS and mixed on a Vortex mixer. The specimens were stored at −20° C. until used. The exact amount of secretion was estimated by weighing the tube before and after collection. Before use they were centrifuged to remove debris. Samples were collected regardless of day in the menstrual cycle excluding only actual days of menstruation. Blood-stained specimens were discarded.

BPV had been purified as follows: Bovine cutaneous warts stored in glycerolphosphate-buffered saline (1:1) at +4° C. were homogenized in 0.1M Tris-HCl, pH 7.5 in an ultra turrax mixer. A 10% suspension was prepared and, after addition of tareosyl and freon, the suspension was centrifuged at 11.950 g for 30 min in a Sorvall SS-34 rotor. The resulting supernatant was centrifuged at 35,000 rpm for 60 min in an MSE 8×40 ml titanium rotor. The pellet was suspended in 0.1M Tris-HCl and mixed with CsCl. The solution was centrifuged to equilibrium at 35,000 rpm in an MSE SW50 rotor overnight. The virus bands were collected, dialyzed against TE buffer (0.01M Tris-HCl, 0.001M EDTA) and stored frozen at −70° C. Extracts of cutaneous warts were purified by 2 cycles of equilibrium centrifugation in CsCl. Two distinct bands were seen in the gradients. The lighter band had a buoyant density of 1.29 g/ml; it consisted of empty virus particles as determined by electron microscopy (EM). The heavy band had a buoyant density of 1.34 g/ml and contained complete virus particles with a typical papovavirus morphology also as determined by EM.

Hyper-immune sera against purified bovine papillomaviruses had been prepared in rabbits by intramuscular inoculation of approximately 100 μg of purified virus, emulsified in Freund's complete adjuvant (Difco laboratories, Detroit, Mich.). Two subsequent inoculations were made two weeks apart, using the same amount of virus but without adjuvant. The rabbits were bled 1 week after the last inoculation.

A modification of previously described ELISA methods was used. Briefly, BPV virions diluted in PBS were added to a 96-well microtitration plate and kept overnight at +4° C. at a fixed concentration of 0.06 μg/well. After three washes with PBS containing 0.05% Tween (PBS-Tween), the plates were blocked with 4% bovine serum albumin (BSA) and 0.1 gelatin in PBS for 6 hours at room temperature, then left overnight at +4° C. Before use, plates were washed 5 times with PBS-Tween. The cervico-vaginal secretions were diluted 1/40 and sera were diluted 1/100 in 4% BSA, 0.1% gelatin and 0.05% Tween. To detect bound antibodies, affinity-purified biotinylated anti-human IgA (alpha chain-specific) or biotinylated anti-human IgG (both from Sigma) were used at a dilution of 1/1000 for 4 hours at room temperature. Peroxidase-conjugated avidin was then added at a dilution of 1/400 for 2 hours at room temperature. As substrate 0.4% o-phenylenediamine (Sigma), 0.012% $H_2O_2$ in 50 mM phosphate-citrate buffer, pH 5.0, was used. Positive controls were rabbit antisera against BPV virions and/or rabbit antisera against elk papillomavirus. Human newborn sera and rabbit pre-immune sera were negative controls.

BPV virions were electrophoresed on a 5–20% polyacrylamide gradient gel. About 5 μg of virions were applied to each sample lane. Transfer to nitrocellulose sheets was done as described by Towbin et al. The sheets were cut into strips and blocked with 2% Tween-80 in 50 mM Tris pH 10.2, 150 mM NaCl, 5 mM $NaN_3$ for 15 minutes. The nitro-cellulose strips were incubated overnight with patients sera diluted 1/100 in wash buffer (50 mM Tris pH 10.2, 150 mM NaCl, 5 mM $Nan_3$, 0.1% Tween-20). After an overnight incubation the blots were washed in the same buffer. Rabbit antiserum against PV was used as positive control and rabbit pre-immune serum as negative control. For detection of bound antibodies biotinylated goat anti-human IgA or biotinylated goat anti-human IgG was used, diluted 1/1000 in wash buffer. The blots were subsequently incubated with peroxidase-conjugated avidin diluted 1/400 in wash buffer. For the rabbit antisera, goat anti-rabbit IgG conjugated to per-oxidase was used, diluted 1/1000 in wash buffer. All blots were developed with 0.02% carbazole (Sigma) in 50 mM sodium acetate, pH 5.5.

FIG. 1 illustrates the detection of IgA antibodies against papillomavirus. The cervical secretions, diluted 1/40, were applied to ELISA plates coated with purified and disrupted BPV virions. IgA antibodies were detected with an IgA-specific biotinylated second antibody and avidin peroxidase conjugate. Following addition of substrate, the absorbances at 490 nm were recorded after 15 minutes. Absorbance values >0.1 above background (human newborn serum) were scored as positive.

IgA antibodies to PV were found in cervical secretions from 17 of 42 women. In the graph of FIG. 1 each point represents the mean absorbance of sample duplicates from each patient. Of 9 women with CIN, 8 had IgA antibodies in their cervical secretions against PV, group I (patients with histologically confirmed intra-epithelial neoplasia, CIN). Koilocytosis in Pap smear and colposcopically verified condylomas without CIN were found in 9 patients, and 3 of those had IgA antibodies against PV, group II (patients with koilocytosis and/or condyloma but no histological evidence of CIN). Six of 24 women with normal examination results had IgA antibodies against PV, group III (patients without any pathological findings). The IgA ELISA absorbances were tested for significant differences among the three groups. In a three-way nonparametric continuous test (Kruskal-Wallis test), the CIN group had significantly higher absorbance values than the normal control group ($p<0.015$). The proportion of IgA positive cervical secretions was also found to be significantly higher in the CIN group (8 of 9) than in the normal group (6 of 24), ($p<0.005$, $Chi^2$-test). By contrast, there was no difference between the group with condylomas/koilocytosis and the normal group ($p>0.05$; absorbance mean $=0.109$ versus $0.104$).

For 15 patients IgG and IgA levels in serum (diluted 1/1000) and secretions (diluted 1/40), were compared. The IgA antibody levels in serum and secretions were relatively well correlated: $p<0.001$, as shown in FIG. 2. The levels of IgG antibodies in serum and secretions were not significantly correlated: $0.05<p<0.1$ as shown in FIG. 3. No significant correlation ($p>0.1$) was found between IgA and IgG levels in secretions as shown in FIG. 4, or in serum (not shown).

In order to investigate which virion polypeptides the PV antibodies were directed against, immunoblotting of the purified BPV virions was performed.

Reference is made to FIGS. 5 and 6. The purified BPV virions were electrophoresed on a 5–20% polyacrylamide gel and transferred to nitro-cellulose. Strips were incubated with rabbit hyper-immune serum against purified bovine virions (+), human newborn serum (−) and 10 patient sera (1 to 10). Bound antibodies were detected with biotinylated goat anti-human IgG (FIG. 5) or biotinylated goat anti-human IgA (FIG. 6) and peroxidase-conjugated avidin. In the IgA test, strips with patient sera No. 2–9 were equally negative as serum No. 1 and are not shown. In FIGS. 5 and 6 the arrows denote the major PV proteins detected, K=molecular weight in kilodalton, and MW=molecular weight markers. The molecular weights of the markers were 200, 116, 92, 66, 44 and 29 kilo-daltons (kDa).

Rabbit hyperimmune sera prepared against the purified bovine virions detected four polypeptides: a major 14-kDa protein, 28-kDa and 54-kDa proteins, and a 64-kDa protein, FIG. 4. Ten of ten tested patients had serum IgG antibodies to the 54-kDa protein. Two patients had serum IgG antibodies to the 64-kDa protein and 2 patients had serum antibodies to the 28-kDa protein. When tested with the IgA-specific conjugate, only one out of ten patient sera had detectable IgA antibody levels in immunoblotting, FIG. 6. This serum had an exceptionally high IgA anti-BPV reactivity as determined by ELISA (compare FIG. 2). In immunoblotting it reacted with the 14-kDa, the 28-kDa and the 54-kDa polypeptides and weakly with the 64-kDa polypeptide (FIG. 6).

It has been shown that local genital tract papilloma virus antibodies exist and can be readily detected and measured. There was found a strong correlation between the presence of IgA antibodies to PV in cervical secretions and the histological diagnosis of CIN. However, 6 of 24 women with normal Pap-smear and colposcopy also had IgA antibodies against PV. It is not known if the patients with IgA antibodies but no CIN may have had histologically undetected CIN lesions. A previous study has suggested that IgG antibodies to the papilloma virus group-specific antigen are elevated in CIN. However, serum IgG antibody levels to PV were also elevated in patients with cutaneous warts. This problem was overcome by measuring only those antibodies that are related to genital tract PV infection, by measuring the IgA antibodies described here. It should be emphasized that the herein described test was found to have no correlation to the previously described test using IgG antibodies. This is concluded from our demonstration that there is correlation between IgA antibodies to HPV in serum and secretions (FIG. 2) but no correlation between IgA and IgG antibodies to HPV in secretions (FIG. 4) or in serum (Table 1). There was a correlation between the levels of IgA antibodies in serum and secretions. It is therefore possible that IgA antibodies in serum may provide a genital-tract specific test that could easily be applied as part of a clinical routine.

The finding that the normal subjects and the patients with evidence of viral replication (koilocytosis and/or condyloma) had IgA antibody levels similar to those of normal subjects may seem surprising. However, this situation is also found for the Epstein-Barr virus, where anti-virus capsid IgA antibodies are not related to the level of virus production but only to the presence of virus-associated cancer. Immunoblotting detected four virion-associated polypeptides. The presence of IgG antibodies to a 54-kDa protein is in accordance with previous studies: A 56-kDa regularly IgG-immunogenic protein encoded by the L1 open reading frame has been identified as a major component of the capsid. A minor approximately 70-kDa capsid protein is encoded by the L2 open reading frame. This protein should correspond to the 64-kDa protein detected by us. The identities of the 28-kDa protein and the 14-kDa proteins are not known. The single IgA-positive serum had an IgA response to the 54-, 28- and 14-kDa polypeptides, whereas the IgG response of the same serum was only directed against the 54-kDa polypeptide. This shows that the PV epitopes which give rise to IgA and IgG are not always identical.

In order to analyse the serum antibody response to the group-specific PV capsid antigens, the prevalence of serum antibodies against PV in a normal, healthy population compared to the serum antibody titers in sera from women with CIN or cervical carcinoma was studied.

A total of 139 control sera from healthy, adult women were obtained. 62 sera were from women attending gynecology outpatient clinics. The women either had no pathological findings (48 women) or had condyloma, but no histopathological evidence of CIN (14 women). 59 sera were obtained from healthy, female laboratory workers and 18 sera from women attending an annual health check-up.

The patient group consisted of 114 women with untreated, histopathologically confirmed cervical neoplasia, of which 13 lesions were classified as CIN 1, 16 lesions were CIN 2, 6 lesions were CIN 3 and the remaining 69 lesions were invasive cervical carcinoma. 83 sera from children at various ages, as well as from adults of both sexes also were obtained.

Virus isolation and purification had been performed as described above.

The preparation of the bovine papillomavirus is shown in FIG. 5 and 6 to consist of four proteins all of which contain epitopes immunoreactive with human sera as shown by immunoblotting.

Purified BPV was disrupted by five cycles of freeze-thawing and diluted in 10 mM carbonate buffer, pH 9.6 and added to half-area 96-well microtiter plates at a fixed concentration of 0.15 µg/well. The plates containing the BPV were kept at room temperature over night. After one wash with PBS-0.05% Tween 20 (PBS-T) the plates were blocked with 10% lamb serum (heat inactivated; Flow) in PBS and incubated for 60 minutes at 37° C. The blocking solution was then discarded and the plates tapped thoroughly against paper. Human sera were diluted 1:20 in 10% lamb serum/PBS, added to the plates in duplicate wells and allowed to react for 120 minutes at 37° C. The plates were then washed five times with PBS-T. To detect bound antibodies there was used a horseradish peroxidase labeled monoclonal antibody against human IgA (Janssen) (FIG. 3) diluted 1:500 in 10% lamb serum/PBS incubated on the plates for 120 minutes at 37° C. The plates were then washed five times with PBS-T and developed with 20 mg/ml 2,2'-azino-di (3-ethylbenzthiazolinsulfonate (6)) deammonium salt (ABTS) diluted 1:50 in 0.1M citrate buffer, pH 4 with 0.9% hydrogen peroxide. The absorbances were recorded at 415 nm after 30 minutes (FIGS. 7, 8) or 60 minutes (FIGS. 9–12). For detection of IgG, the plates were washed and blocked with 10% lamb serum-PBS for 60 minutes at 37° C.

Then, there was used a rabbit anti-human IgG-alkaline phosphatase conjugate (Dako) diluted 1:1000 in 10% lamb serum PBS for 120 minutes at 37° C. (FIG. 9–12) or a horseradish peroxidase conjugated monoclonal antibody against human IgG (Janssen), diluted 1:2000 (FIG. 7, 8). After washing five times with PBS-T, 1 mg/ml phosphatase substrate (Sigma) in 0.1M diethanolamine buffer, pH 9.6/1 mM MgCl$_2$ was added and the plates were read at 405 nm after 90 minutes. When the peroxidase-conjugated antibody was used, the plates were developed for 30 minutes as described above for the IgA conjugate. For detection of IgM antibodies, the plates were washed and blocked as described above and then incubated with an anti-human IgM-glucose oxidase conjugate (Sera-lab) at dilution 1:800 in 10% lamb serum/PBS for 120 minutes. 0.36 mg/ml of ABTS, 2.4% glucose, 8 µg/ml horseradish peroxidase (Sigma) in 0.1M phosphate buffer, pH 6.0, was used as substrate. The plates were read at 415 nm after 60 minutes. For all ELISAs an absorbance of 0.15 or more above background (same serum on uncoated wells) was considered a positive reaction. Two CIN patient sera with known reactivity were used as internal standards in all tests. As negative control served uncoated wells in duplicates.

The mean of duplicate absorbances, with mean of duplicate absorbances on uncoated wells subtracted, were analysed for statistically significant differences between the patient group and the healthy control group by a two-sided, non-parametric ranking test (Mann-Whitney test).

The results were as follows:

Of 83 sera from a normal population consisting of both children and adults of both sexes, 24 had IgA antibodies and 46 had IgG antibodies against PV. The IgA anti-BPV titers were found to be elevated (p<0.002, Mann-Whitney test) in healthy males compared to healthy females as illustrated in FIG. 7, which shows age and sex-related distribution of serum IgA antibodies to PV in a normal population. Sera were diluted 1:20 and IgA antibodies against BPV were detected with an alpha-chain specific horseradish peroxidase conjugated at monoclonal antibody. Following addition of substrate, the absorbances at 415 nm were recorded after 30 minutes. Each point represents the mean absorbance of sample duplicates with mean of duplicate blanks subtracted for each patient. The IgA antibody levels were very similar in children (<20 years) as compared to adults, both for males and females (mean for adults 0.79; mean for children 0.103). The same sera tested for IgA antibodies against BPV were also tested for the presence of IgG antibodies according to FIG. 8, which shows age and sex-related distribution of serum IgG antibodies to PV in a normal population. The same sera tested for IgA antibodies against BPV were tested for the presence of IgG antibodies in a similar way as in FIG. 7 except that an anti-IgG horseradish peroxidase conjugated monoclonal antibody was used. The IgG antibodies were strongly elevated in children as compared to adults ($p<0.0015$). There was also a tendency, however not significant, that IgG anti-BPV titers were elevated in normal males as compared to females ($0.1>p>0.05$).

One-hundred and thirty-nine sera from healthy adult women, 13 sera from women with CIN grade 1, 16 sera from women with CIN grade 2, 16 sera from women with CIN grade 3 and 69 sera from women with invasive squamous cell carcinoma of the cervix uteri (SCC) were analyzed for IgA, IgG and IgM antibodies to PV. For the statistical analysis the different CIN groups and the SCC group were combined to one single cervical neoplasia group. The IgA antibody levels were significantly increased in the CIN or carcinoma patient group, compared to the age and sex matched controls without known CIN ($p<0.025$) as shown in FIG. 9, wherein detection of IgA antibodies against PV in serum from patients with CIN or carcinoma of the cervix uteri is illustrated. Sera were diluted 1:20 and added to plates coated with BPV. IgA antibodies were detected with a horseradish peroxidase labeled monoclonal antibody against human IgA. After the addition of substrate the absorbances were read at 415 nm after 60 minutes. Each point represent the mean absorbance of duplicates with mean of duplicate for serum blanks subtracted. Compared to the "No CIN" group, the titers in the CIN and carcinoma group are elevated ($p<0.025$).

The IgG antibody titers against PV were significantly decreased in cervical neoplasia patients compared to controls ($p<0.001$) as illustrated in FIG. 10, illustrating detection of IgG antibodies to PV in serum from patients with CIN or carcinoma of the cervix uteri. Same sera as in FIG. 9 were tested for the presence of IgG antibodies against BPV using a rabbit anti-human IgG-alkaline phosphatase conjugate. After addition of substrate the absorbances were recorded at 405 nm after 90 minutes.

There was also a significant decrease in the IgM titers to PV in the cervical neoplasia patient group compared to the controls ($p<0.005$) according to FIG. 11, which illustrates the detection of IgM antibodies to PV in serum from patients with CIN or carcinoma of the cervix uteri. Same sera as in FIG. 9 were also tested for the presence of IgM antibodies against PV. As conjugate an anti-human IgM glucose oxidase conjugate was used and after development the plates were read at 415 nm after 60 minutes. When the difference between the IgA and IgG response (IgA-IgG) was compared for the group without known CIN and the CIN or carcinoma group, a striking elevation for the CIN or carcinoma patient group was noted ($p<0.0001$). FIG. 12 illustrates the difference between the IgA and IgG response (IgA-IgG) to PV in relation to disease. Same absorbance values as recorded in FIGS. 9 and 10 were plotted as IgA subtracted with IgG.

All HPV genomes have at least eight potentially protein-encoding regions, open reading frames (ORFs). Two ORFs, L1 and L2, have been demonstrated to encode viral capsid proteins. The L1 protein is an approximately 54 kDa abundant capsid protein that is regularly immunogenic for both IgG and IgA antibodies. Antibodies to the L1 protein have virus-neutralizing activity, at least for BPV-1. Several studies using monoclonal antibodies or bacterially expressed fusion proteins have shown that the L1 protein both has epitopes in common for all types of PV, the so-called group-specific epitopes, as well as epitopes specific for each HPV type. One group-specific and One type-specific epitope of L1 in HPV 6 have been mapped using a set of small fusion proteins. The L2 ORF encodes an approximately 70 kDa capsid protein, by us referred to as the approximately 64-kDa protein, that is comparatively low in abundance. The L2 protein has been reported to contain type-specific epitopes. In order to obtain a more complete map of the linear epitopes of the HPV 16 major capsid proteins, the entire amino acid sequences of these two proteins were synthesized as a set of 20 amino acids synthetic peptides with 5 amino acids overlap. The positions of the sequence-specific epitopes that reacted with IgA, IgG or IgM antibodies in the sera from patients with HPV 16-carrying cervical neoplasia are reported in FIG. 13–19.

Sixty-six 20 amino acids peptides with a 5 amino acids overlap to each other were synthesized according to the deduced amino acid sequence of the L1 and L2 ORFs of HPV 16. For denoting the position in the protein, the putative initiation codon was assigned to be amino acid number 1. Synthetic peptide number 1 corresponds to amino acids 2–21 in the L1 ORF, peptide number 2 to amino acids 17–36, number 3 to amino acids 32 to 51 and so on until the L1 carboxy-terminal peptide (number 35) which corresponds to amino acids 512–531. Peptide number 36 corresponds to the amino terminus of the L2 ORF (amino acids 2–21), number 37 is amino acids 17–36 and so on. The two peptides at the L2 carboxyterminus (number 65 and 66) were synthesized as 21 residues peptides, resulting in that their amino acid positions are 437–457 and 453–473, respectively. The amino acid sequences of the most immunoreactive peptides are listed in table 2. The symbols therein are explained by table 3. The amino acid sequences of all peptides used in FIG. 13–19 are shown in table 4. Peptides were synthesized using t-Boc amino acids (Bachem AG, Bubendorf, Switzerland) and p-methylbenzhydrylamine resin (Fluka AG, Buchs, Switzerland) according to the multiple solid phase peptide synthesis method. Removal of the protecting groups from the formyltryptophane and methionine sulfoxide residues was achieved by cleavage with 25% hydrogen fluoride. The peptides were then cleaved from the resin with liquid hydrogen fluoride using a multi-vessel apparatus.

Sixty-four sera from patients with either carcinoma in situ (CIN grade 3) or invasive cervical carcinoma were obtained. The corresponding cervical biopsies had been analyzed for presence of HPV DNA either by Southern blot (32 cases) or by dot-blot (32 cases) hybridization with 32-P-labelled probes of cloned HPV 16 and HPV 18, as described. HPV 16 had been detected in 32 cases and HPV 18 in 4 cases. Thirty sera from the patients with HPV 16 carrying cervical neoplasia were available in sufficient amounts to be tested with all the different synthetic peptides.

22 sera from patients with other tumors were obtained. 38 sera were obtained from healthy women.

The synthetic peptides were diluted in 10 mM carbonate buffer, pH 9.6 and added to half-area 96-well microtiter plates (Costar) at a concentration of 20 µg peptide/ml. The plates were kept at room temperature over night. After one wash with PBS-0.05% Tween 20 (PBS-T) the plates were blocked with 10% lamb serum (heat inactivated; Flow) in PBS and incubated for 60 minutes at 37° C. The blocking solution was then discarded and the plates tapped thoroughly against paper. Human sera were diluted 1:30 in 10% lamb serum/PBS, added to the plates and allowed to react for 120 minutes at 37° C. The plates were then washed five times with PBS-T. To detect bound antibodies there was a horseradish peroxidase labeled monoclonal antibody against human IgA diluted 1:500 in 10% lamb serum/PBS incubated on the plates for 120 minutes at 37° C. The plates were then washed five times with PBS-T and developed with 20 mg/ml 2,2'-azino-di (3-ethylbenzthiazolinsulfonate (6)) deammonium salt (ABTS) diluted 1:50 in 0.1M citrate buffer, pH 4 with 0.9% hydrogen peroxide. The absorbances were recorded at 415 nm after 60 minutes. For detection of IgG, the plates were washed and blocked with 10% lamb serum-PBS for 60 minutes at 37° C. Thereafter, a rabbit anti-human IgG-alkaline phosphatase conjugate (Dako), diluted 1:1000 in 10% lamb serum-PBS, was applied for 120 minutes at 37° C. After washing five times with PBS-T and once with 0.1M diethanolamine buffer, pH 9.6, 1 mg/ml phosphatase substrate (Sigma) in 0.1M diethanolamine buffer, pH 9.6/1 mM $MgCl_2$ was added and the plates were read at 405 nm after 90 minutes. For detection of IgM antibodies, the plates were washed and blocked as described above and then incubated with an anti-human IgM-glucose oxidase conjugate (Seralab), at dilution 1:800 in 10% lamb serum-PBS, for 120 minutes. As substrate there was used 0.36 mg/ml of ABTS, 2.4% glucose, 8 µg/ml horseradish peroxidase (Sigma) in 0.1M phosphate buffer, pH 6.0. The plates were read at 415 nm after 60 minutes. An absorbance of 0.1 or more above background (same serum on uncoated wells) was considered a positive reaction. As an internal standard, the 30 HPV 16-positive sera were in each test reacted with the known antigenic peptide HKSAIVTLTYDSEWQRDQC (SEQ ID NO. 67) from the E2 ORF of HPV 16. The ELISA absorbances were adjusted relative to the internal standard to compensate for possible inter-assay variation.

The ELISA absorbances, with absorbances of the same serum reacted with uncoated wells subtracted, were analysed for statistically significant differences between the HPV 16-carrying cervical neoplasia patient group and the control group by a two-sided, non-parametric ranking test (Mann-Whitney test).

The complete amino acid sequence of the L1 and L2 proteins of HPV type 16 were synthesized as a set of 66 synthetic peptides, 20 amino acids long and with a 5 residues overlap to each other. All peptides were tested in ELISA for reactivity with either IgA, IgG or IgM antibodies in 30 sera from HPV 16-carrying cervical neoplasia patients. Several regions of the L1 protein were regularly reactive with IgA antibodies present in these sera as illustrated in FIG. 13, which shows IgA reactivity to the L1 protein. Each point represents the absorbance value (OD) for one serum reacted with the peptide whose number is given below the abscissa. The absorbance value for the same serum when reacted with uncoated wells has been subtracted. Thirty sera from patients with HPV 16-carrying cervical neoplasia were diluted at 1:30 and reacted with 35 twenty residues synthetic peptides representing the entire amino acid sequence of the L1 ORF of HPV 16. Bound IgA antibodies were detected with an IgA (alpha-chain)-specific enzyme conjugated monoclonal antibody. The IgA response was especially strong against the peptides deduced from an internal region of the protein spanning amino acids 167 up to 271, corresponding to peptides 12-18. Outside this major immunoreactive region there were several additional immunoreactive epitopes, notably the amino terminus of the protein (peptide 1), peptide 8 (amino acids 102-121) and several epitopes positioned on the carboxyterminal side of the major immunoreactive region, notably peptides 21 and 31 (corresponding to amino acids 302-321 and to 452-471, respectively).

In contrast, very few peptides deduced from the L2 protein were reactive with IgA antibodies in these sera as shown in FIG. 14, which shows IgA reactivity to the L2 protein. Similar experiment as in FIG. 13, except that the sera were reacted with 31 twenty residues synthetic peptides representing the entire amino acid sequence of the L2 ORF of HPV 16. The major epitope was positioned in the middle of the protein (peptide 49, amino acids 197-216). Other epitopes were also detected in the amino-terminal part of the protein (peptides 37-38, amino acids 17-41), whereas the carboxyterminal part of L2 was less reactive. The IgG reactivity of the L1 protein was less than the IgA reactivity. Reference is made to FIG. 15, which shows IgG reactivity to the L1 protein. Similar experiment as in FIG. 13, except that an IgG (gamma-chain)-specific enzyme conjugated rabbit antibody was applied. Although the major IgA-immunoreactive region (peptides 12-18) was also immunoreactive with IgG antibodies, the IgG reactivity was equally strong also with several epitopes outside this region, e.g. with peptide 24 (amino acids 347-366).

The L2 protein had a few IgG-reactive epitopes as illustrated in FIG. 16, which shows IgG reactivity to the L2 protein. Similar experiment as in FIG. 13, except that an IgG (gamma-chain)-specific enzyme conjugated rabbit antibody was applied and that the sera were reacted with 31 twenty residues synthetic peptides representing the entire amino acid sequence of the L2 ORF of HPV 16. This resembles what we found for the IgA reactivity of this protein. Peptide 49, which was the major IgA reactive epitope of this protein, was also found to be the major IgG-reactive epitope. The IgA-reactive epitope at the aminoterminus of L2 (peptides 37-38) was also found to be IgG-reactive (FIG. 4). The IgM reactivity to the L1 protein was scattered among several epitopes along the entire length of the protein as illustrated in FIG. 17, which shows IgM reactivity to the L1 protein. Similar experiment as in FIG. 13, except that an IgM (mu-chain)-specific enzyme conjugated goat antibody was applied. Interestingly, the main IgM reactivity was found against peptides that were not very immunoreactive with IgG or IgA antibodies, e.g. peptides 9, 13 and 23 (amino acid positions 122-142, 182-202 and 332-352).

The IgM immunoreactivity of the L2 protein resembled that for the IgA and IgG in that the L2 peptides were much less reactive than the L1 peptides. Reference is made to FIG. 18, which shows IgM reactivity to the L2 protein. Similar experiment as in FIG. 13, except that an IgM (mu-chain)-specific enzyme conjugated goat antibody was applied and that the sera were reacted with 31 twenty residues synthetic peptides representing the entire amino acid sequence of the L2 ORF of HPV 16. Actually, not a single L2 peptide was immunoreactive with IgM in more than 4 out of 30 sera. The seven most immunoreactive peptides (peptides 8, 12, 13, 14, 16, 17, and 24) were also tested for IgA, IgG and IgM reactivity with a panel of 60 control sera, of which 22 were obtained from patients with irrelevant tumors and 38 were obtained from healthy donors. Most of these peptides showed significant immunoreactivity only with less than 10% of these control sera as illustrated in FIG. 19, which shows disease-associated reactivity of synthetic peptides. Four of the highly immunoreactive synthetic peptides that had striking differences in reactivity between 30 HPV-16-carrying cervical neoplasia sera (HPV 16 SCC) and a control group of 60 sera from patients with other tumors or from healthy donors (Control) are shown in FIG. 19. Each point denotes the absorbance value in ELISA with the absorbance value on uncoated wells subtracted. A high sensitivity for detection of HPV 16-carrying cervical neoplasia was seen with the IgM reactivity to peptide 8:70%. The specificity of this test was 95% (3/60 control sera were reactive). The IgG reactivity to peptide 24, showed a high specificity: 97% (2/60 control sera were reactive), but a lower sensitivity, 53% (16/30 patient sera reacted). The IgA reactivities to peptides 14 and 16 both had sensitivities around 60% and specificities just above 90% (FIG. 19), and the immunoreactivity among the positive sera was among the highest detected (compare FIGS. 1–6).

By showing that a peptide is immunoreactive, the inventors have defined that it contains an epitope reactive with human sera. The epitope contained within this peptide sequence is not absolutely dependent on the exact sequence of the peptide, but can also be contained in a variety of minor modifications of the original peptide. Such modifications include extensions, truncations, cyclizations and amino acid substitutions. Sometimes the question arises if such a modified peptide should be considered a new peptide containing a new epitope. By competitive immunoassays with the original peptide and the modification thereof, it is straightforward to determine if the modified peptide is substantially immunoreactive with antibodies to the original peptide and thus contains the same epitope. It should be emphasized that a peptide can be produced in many different ways. Herein peptide synthesis by organic chemistry methods has been used, but the same peptides can also be produced by many other means for example by recombinant DNA expression systems.

It is understood that the herein contained description of the methods is intended to exemplify, but not limit, the present invention. An immunoassay can for example be performed in a variety of different ways. Detection of the antibodies that have bound to the specific antigen can for example be achieved with various antibodies to antibodies (anti-antibodies) or other compounds with affinity for antibodies, such as protein A or protein G. These reagents can be labelled in many different ways, for example radioactively (radioimmunoassay), with fluorescein (fluoroimmunoassay) or enzymatically (enzyme-linked immunoassay, ELISA or EIA). A special case of enzymatic immunoassay is when the antigen-antibody complexes are detected on tissue sections. Such a procedure is instead referred to as immunostaining or immunohistocytochemistry, although the underlying principle is the similar as for ELISA.

An ELISA procedure can also be carried out in a variety of formats. Methods for enhancement of ELISA sensitivity using several layers of anti-antibodies, avidin-biotin complexes and enzyme-anti-enzyme antibody complexes are well known in the art. The solid support for fixation of antigen is usually plastic, as described here, but a variety of other solid supports such as latex or agarose have been described. It is also not necessary for the antigen to be directly fixed onto the solid support. There is for example a commonly used ELISA format that fixes the specific antigen to the solid support via a solid-phase-fixed antibody to the antigen, so-called catching antibody ELISA or sandwich ELISA.

A special case of immunoassay which involves a blotting (transfer) of antigen to a solid support in sheet format is termed immunoblotting. Typically, the solid support is nitrocellulose or nylon sheets, but other supports have been described. It is also a typical feature of this method that, prior to blotting, the antigens are separated according to size by gel electrophoresis or similar methods. Detection of antibodies bound to the specific antigen on the sheet can be carried out in similar ways as for other immunoassays. The here described detection using an anti-antibody, a biotin-avidin complex enhancement step and an enzymatic labelling is just one example of such a detection.

For diagnostic methods in general it is well known that a combination of several diagnostic methods produces a diagnostic method with better sensitivity and/or specificity than the individual tests contained in the combination. It is self-evident that any of the here described antibody tests could be combined with each other, or with other tests, to produce a combined diagnostic test with optimal sensitivity and specificity.

TABLE 1

| | E490 | |
|---|---|---|
| | serum | secretions |
| IgG | | |
| 19084 | .368 | .184 |
| 19085 | .592 | .173 |
| 19086 | 1.041 | .306 |
| 19087 | .230 | .073 |
| 19088 | .770 | .188 |
| 19089 | .240 | .180 |
| 19090 | .253 | .294 |
| 19091 | .210 | .032 |
| 19092 | .198 | .060 |
| 19093 | .660 | .195 |
| 19094 | .945 | .281 |
| 19095 | .224 | .228 |
| 19096 | .280 | .278 |
| 19097 | .259 | .226 |
| 19098 | .222 | .134 |
| IgA | | |
| 19084 | .298 | .090 |
| 19085 | .199 | .072 |
| 19086 | .327 | .131 |
| 19087 | .137 | .056 |
| 19088 | .235 | .118 |
| 19089 | .140 | .053 |
| 19090 | .153 | .070 |
| 19091 | .122 | .076 |
| 19092 | .119 | .062 |
| 19093 | 1.021 | .394 |
| 19094 | .140 | .066 |
| 19095 | .073 | .099 |
| 19096 | .136 | .098 |
| 19097 | .128 | .096 |
| 19098 | .098 | .050 |

Measurement of IgA and IgG antibodies to PV in serum and secretions. Extinction coefficients from ELISA results based on 15 patients. Part of this information is depicted in FIGS. 2, 3 and 4. Statistical analysis of the data show that measurement of IgA antibodies to PV, either in serum or secretions, is a test that is not correlated to the previously described test for IgG antibodies to PV, either in serum or secretions.

TABLE 2

| Peptide No. (SEQ ID NO:) | Peptide sequence | IgA | IgG | IgM |
|---|---|---|---|---|
| 8 | NKFGFPDTSFYNPDTQRLVW | <0.05 | <0.0001 | <0.0001 |
| 12 | VDNRECISMDYKQTQLCLIG | <0.002 | <0.0001 | <0.01 |
| 13 | LCLIGCKPPIGEHWGKGSPC | <0.02 | <0.0001 | NS |
| 14 | KGSPCTNVAVNPGDCPPLEL | <0.0005 | <0.0001 | <0.0001 |
| 16 | VHTGFGAMDFTTLQANKSEV | <0.0001 | <0.0001 | <0.0001 |
| 17 | NKSEVPLDICTSICKYPDYI | <0.01 | NS | <0.0001 |
| 24 | NGICWGNQLFVTVVDTTRST | <0.002 | <0.0001 | <0.001 |

Detection of significantly elevated antibody titers against HPV 16 synthetic peptides among sera from 30 patients with HPV 16-carrying cervical neoplasia as compared to a control group of 60 sera from patients with other tumors or from healthy donors. Figures denote the p-values for significant differences among these two parameters (Mann-Whitney test).
NS = Not significant

TABLE 3

| SYMBOL | | AMINO ACID |
|---|---|---|
| 1-Letter | 3-Letter | |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Try | L-tryptophan |
| R | Arg | L-arginine |
| D | Asp | L-aspartic acid |
| N | Asn | L-asparagine |
| C | Cys | L-cysteine |

TABLE 4

Amino acid sequences of the synthetic peptides used in the experiments depicted in FIGS. 13–19

| Pep No.(SEQ ID NO:) | Sequence | Pep No. | Sequence |
|---|---|---|---|
| 1 | QVIFIYILVITCYENDVNVY | 41 | TRPPTATDTLAPVRPPLTVD |
| 2 | DVNVYHIFFQMSLWLPSEAT | 42 | PLTVDPVGPSDPSIVSLVEE |
| 3 | PSEATVYLPPVPVSKVVSTD | 43 | SLVEETSFIDAGAPTSVPSI |
| 4 | VVSTDEYVARTNIYYHAGTS | 44 | SVPSIPPDVSGFSITTSTDT |
| 5 | HAGTSRLLAVGHPYFPIKKP | 45 | TSTDTTPAILDINNTVTTVT |
| 6 | PIKKPNNNKILVPKVSGLQY | 46 | VTTVTTHNNPTFTDPSVLQP |
| 7 | SGLQYRVFRIHLPDPNKFGF | 47 | SVLQPPTPAETGGHFTLSSS |
| 8 | NKFGFPDTSFYNPDTQRLVW | 48 | TLSSSTISTHNYEEIPMDTF |
| 9 | QRLVWACVGVEVGRGQPLGV | 49 | PMDTFIVSTNPNTVTSSTPI |
| 10 | QPLGVGISGHPLLNKLDDTE | 50 | SSTPIPGSRPVARLGLYSRT |
| 11 | LDDTENASAYAANAGVDNRE | 51 | LYSRTTQQVKVVDPAFVTIP |
| 12 | VDNRECISMDYKQTQLCLIG | 52 | FVTTPTKLITYDNPAYEGID |
| 13 | LCLIGCKPPIGEHWGKGSPC | 53 | YEGIDVDNTLYFSSNDNSIN |
| 14 | KGSPCTNVAVNPGDCPPLEL | 54 | DNSINIAPDPDFLDIVALHR |
| 15 | PPLELINTVIQDGDMVHTGF | 55 | VALHRPALTSRRTGIRYSRI |
| 16 | VHTGFGAMDFTTLQANKSEV | 56 | RYSRIGNKQTLRTSGKSIG |
| 17 | NKSEVPLDICTSICKYPDYI | 57 | GKSIGAKVHYYYDLSTIDPA |
| 18 | YPDYIKMVSEPYGDSLFFYL | 58 | TIDPAEEIELQTITPSTYTT |
| 19 | LFFYLRREQMFVRHLFNRAG | 59 | STYTTTSHAASPTSINNGLY |
| 20 | FNRAGTVGENVPDDLYIKGS | 60 | NNGLYDIYADDFITDTSTTP |
| 21 | YIKGSGSTANLASSNYFPTP | 61 | TSTTPVPSVPSTSLSGYIPA |
| 22 | YFPTPSGSMVTSDAQIFNKP | 62 | GYIPANTTIPFGGAYNIPLV |

TABLE 4-continued

Amino acid sequences of the synthetic peptides used in the experiments depicted in FIGS. 13–19

| Pep No.(SEQ ID NO:) | Sequence | Pep No. | Sequence |
|---|---|---|---|
| 23 | IFNKPYWLQRAQGHNNGICW | 63 | NIPLVSGPDIPINITDQAPS |
| 24 | NGICWGNQLFVTVVDTTRST | 64 | DQAPSLIPIVPGSPQYTIIA |
| 25 | TTRSTNMSLCAAISTSETTY | 65 | YTIIADAGDFYLHPSYYMLRK |
| 26 | SETTYKNTNFKEYLRHGEEY | 66 | YMLRKRRKRLPYFFSDVSLAA |
| 27 | HGEEYDLQFIFQLCKITLTA | 67 | HKSAIVILTYDSEWQRDQC |
| 28 | IILTADVMTYIHSMNSTILE | | |
| 29 | STILEDWNFGLQPPPGGTLE | | |
| 30 | GGTLEDTYRFVTQAIACQKH | | |
| 31 | ACQKHTPPAPKEDDPLKKYT | | |
| 32 | LKKYIFWEVNLKEKFSADLD | | |
| 33 | SADLDQFPLGRKFLLQAGLK | | |
| 34 | QAGLKAKPKFILGKRKATPT | | |
| 35 | KATPTTSSTSTTAKRKKRKL | | |
| 36 | RHKRSAKRTKRASATQLYKT | | |
| 37 | QLYKTCKQAGTCPPDIIPKV | | |
| 38 | IIPKVEGKTIAEQILQYGSM | | |
| 39 | QYGSMGVFFGGLGIGTGSGT | | |
| 40 | TGSGTGGRTGYIPLGTRPPT | | |

We claim:

1. A diagnostic method for detecting infection with papillomavirus (PV) in a body fluid or tissue which is useful for diagnosing PV-associated neoplasia, which comprises:

a) reacting serum or other body fluid with papillomavirus protein selected from a group consisting of the L2-encoded approximately 64 kDa papillomavirus protein, the L1-encoded approximately 54 kDa papillomavirus protein, an approximately 28 kDa papillomavirus virion protein and an approximately 14 kDa papillomavirus virion protein; said papillomavirus protein having a sequence which is immunologically reactive with the antibody of said virus;

b) forming a complex of said papillomavirus protein and human IgA antibodies; wherein the formation of human IgA antibody/protein complex is a confirmation for the presence of an infection with papillomavirus; and c) detecting said human IgA antibody-protein complex, wherein each protein is an isolated and purified protein.

2. A diagnostic method for detecting infection with papillomavirus (PV) in a body fluid or tissue which is useful for diagnosing PV-associated neoplasia, which comprises:

a) forming an antibody-antigen complex by reacting serum or other body fluid with a late protein peptide which has the same epitope as a peptide having an amino acid sequence represented by a formula selected from the group consisting of:

| | |
|---|---|
| QVIFIYILVITCYENDVNVY | (SEQ ID NO 1), |
| PSEATVYLPPVPVSKVVSTD | (SEQ ID NO 3), |
| VVSTDEYVARTNIYYHAGTS | (SEQ ID NO 4), |
| HAGTSRLLAVGHPYFPIKKP | (SEQ ID NO 5), |
| PIKKPNNNKILVPKVSGLQY | (SEQ ID NO 6), |
| SGLQYRVFRIHLPDPNKFGF | (SEQ ID NO 7), |
| NKFGFPDTSFYNPDTQRLVW | (SEQ ID NO 8), |
| QRLVWACVGVEVGRGQPLGV | (SEQ ID NO 9), |
| VDNRECISMDYKQTQLCLIG | (SEQ ID NO 12), |
| LCLIGCKPPIGEHWGKGSPC | (SEQ ID NO 13), |
| KGSPCTNVAVNPGDCPPLEL | (SEQ ID NO 14), |
| PPLELINTVIQDGDMVHTGF | (SEQ ID NO 15), |
| VHTGFGAMDFTTLQANKSEV | (SEQ ID NO 16), |
| NKSEVPLDICTSICKYPDYI | (SEQ ID NO 17), |
| YPDYIKMVSEPYGDSLFFYL | (SEQ ID NO 18), |
| YIKGSGSTANLASSNYFPTP | (SEQ ID NO 21), |
| YFPTPSGSMVTSDAQIFNKP | (SEQ ID NO 22), |
| IFNKPYWLQRAQGHNNGICW | (SEQ ID NO 23), |
| NGICWGNQLFVTVVDTTRST | (SEQ ID NO 24), |
| TTRSTNMSLCAAISTSETTY | (SEQ ID NO 25), |
| SETTYKNTNFKEYLRHGEEY | (SEQ ID NO 26), |
| ITLTADVMTYIHSMNSTILE | (SEQ ID NO 28), |
| GGTLEDTYRFVTQAIACQKH | (SEQ ID NO 30), |
| ACQKHTPPAPKEDDPLKKYT | (SEQ ID NO 31), |
| LKKYTFWEVNLKEKFSADLD | (SEQ ID NO 32), |
| SADLDQFPLGRKFLLQAGLK | (SEQ ID NO 33), |
| QAGLKAKPKFTLGKRKATPT | (SEQ ID NO 34), |
| QLYKTCKQAGTCPPDIIPKV | (SEQ ID NO 37), |
| IIPKVEGKTIAEQILQYGSM | (SEQ ID NO 38), |
| PMDTFIVSTNPNTVTSSTPI | (SEQ ID NO 49), |
| GKSIGAKVHYYYDLSTIDPA | (SEQ ID NO 57), | and

| | |
|---|---|
| NNGLYDIYADDFITDTSTTP | (SEQ ID NO 60), | and which is immunoreactive with antibodies to the late protein peptide, as determined by competitive immunoassay, in an animal or human infected with papillomavirus, and b) detecting said antibody antigen complex, wherein the formation of mammalian antibody/antigen complex is a confirmation for the presence of an infection with papillomavirus.

3. A method as in claim 1, wherein said antibody-antigen complex is of human origin and the infection to be detected is HPV infection or HPV-associated disease.

4. A method as in claim 2, wherein the presence of said complex is ascertained by immunoassay.

5. A method as in claim 4, wherein the immunoassay is ELISA.

6. A method as in claim 4, wherein the immunoassay is immunoblotting.

7. A method as in claim 2, wherein the detection is effected on a secretion.

8. A method as in claim 7, wherein the detection is effected on cervical secretion.

9. A method as in claim 8, wherein the detection is made for diagnosis of cervical neoplasia.

10. A method as in claim 7, wherein the secretion is taken on a swab, brush, or spatula, and is washed off therefrom in a liquid diluent.

11. A method as in claim 2, wherein the detection is effected on serum.

12. A method as in claim 2, wherein said antibody-antigen complex is an IgG antibody-antigen complex and said late protein peptide has the same epitope as a peptide which has an amino acid sequence represented by a formula selected from the group consisting of:

| | |
|---|---|
| PSEATVYLPPVPVSKVVSTD | (SEQ ID NO 3), |
| VDNRECISMDYKQTQLCLIG | (SEQ ID NO 12), |
| KGSPCTNVAVNPGDCPPLEL | (SEQ ID NO 14), |
| YPDYIKMVSEPYGDSLFFYL | (SEQ ID NO 18), |
| YIKGSGSTANLASSNYFPTP | (SEQ ID NO 21), |
| NGICWGNQLFVTVVDTTRST | (SEQ ID NO 24), |
| TTRSTNMSLCAAISTSETTY | (SEQ ID NO 25), |
| SADLDQFPLGRKFLLQAGLK | (SEQ ID NO 33), |
| QLYKTCXQAGTCPPDIIPKV | (SEQ ID NO 37), |
| IIPKVEGKTIAEQILQYGSM | (SEQ ID NO 38), |
| PMDTFIVSTNPNTVTSSTPI | (SEQ ID NO 49), | and

| | |
|---|---|
| NNGLYDIYADDFITDTSTTP | (SEQ ID NO 60), | which is immunoreactive with antibodies to the late protein peptide, as determined by competitive immunoassay, in an animal or human infected with papillomavirus, wherein the formation of mammalian antibody/antigen complex is a confirmation for the presence of an infection with papillomavirus.

13. A method as in claim 12, wherein said IgG antibody-antigen complex is of human origin and the infection to be detected is HPV infection or HPV-associated disease.

14. A method as in claim 12, wherein the presence of said complex is ascertained by immunoassay.

15. A method as in claim 14, wherein the immunoassay is ELISA.

16. A method as in claim 14, wherein the immunoassay is immunoblotting.

17. A method as in claim 12, wherein the detection is effected on a secretion.

18. A method as in claim 17, wherein the detection is effected on cervical secretion.

19. A method as in claim 18, wherein the detection is made for diagnosis of cervical neoplasia.

20. A method as in claim 19, wherein the secretion is taken on a swab, brush, or spatula, and is washed off therefrom in a liquid diluent.

21. A method as in claim 12, wherein the detection is effected on serum.

22. A method as in claim 2, where said antibody-antigen complex is an IgM antibody-antigen complex and said late protein peptide has the same epitope as a peptide which has an amino acid sequence represented by a formula selected from the group consisting of:

| | |
|---|---|
| HAGTSRLLAVGHPYFPIKKP | (SEQ ID NO 5), |
| PIKKPNNNKILVPKVSGLQY | (SEQ ID NO 6), |
| SGLQYRVFRIHLPDPNKFGF | (SEQ ID NO 7), |
| NKFGFPDTSFYNPDTQRLVW | (SEQ ID NO 8), |
| QRLVWACVGVEVGRGQPLGV | (SEQ ID NO 9), |
| VDNRECISMDYKQTQLCLIG | (SEQ ID NO 12), |
| LCLIGCKPPIGEHWGKGSPC | (SEQ ID NO 13), |
| KGSPCTNVAVNPGDCPPLEL | (SEQ ID NO 14), |
| NKSEVPLDICTSICKYPDYI | (SEQ ID NO 17), |
| YPDYIKMVSEPYGDSLFFYL | (SEQ ID NO 18), |
| YIKGSGSTANLASSNYFPTP | (SEQ ID NO 21), |
| IFNKPYWLQRAQGHNNGICW | (SEQ ID NO 23), |
| TTRSTNMSLCAAISTSETTY | (SEQ ID NO 25), |
| SETTYKNTNFKEYLRHGEEY | (SEQ ID NO 26), |
| ITLTADVMTYIHSMNSTILE | (SEQ ID NO 28), |
| GGTLEDTYRFVTQAIACQKH | (SEQ ID NO 30), |
| ACQKHTPPAPKEDDPLKKYT | (SEQ ID NO 31), |
| and | |
| LKKYTFWEVNLKEKFSADLD | (SEQ ID NO 32), | which is immunoreactive with antibodies to the late protein peptide, as determined by competitive immunoassay, in an animal or human infected with papillomavirus, wherein the formation of mammalian antibody/antigen complex is a confirmation for the presence of an infection with papillomavirus.

23. A method as in claim 22, wherein said IgM antibody-antigen complex is of human origin and the infection to be detected is HPV infection or HPV-associated disease.

24. A method as in claim 22, wherein the presence of said complex is ascertained by immunoassay.

25. A method as in claim 24, wherein the immunoassay is ELISA.

26. A method as in claim 24, wherein the immunoassay is immunoblotting.

27. A method as in claim 22, wherein the detection is effected on a secretion.

28. A method as in claim 27, wherein the detection is effected on cervical secretion.

29. A method as in claim 28 wherein the detection is made for diagnosis of cervical neoplasia.

30. A method as in claim 27, wherein the secretion is taken on a swab, brush, or spatula, and is washed off therefrom in a liquid diluent.

31. A method as in claim 22, wherein the detection is effected on serum.

32. A method as in claim 2, where said antibody-antigen complex is an IgA antibody-antigen complex and said late protein peptide has the same epitope as a peptide which has an amino acid sequence represented by a formula selected from the group consisting of:

| | |
|---|---|
| QVTFIYILVITCYENDVNVY | (SEQ ID NO 1), |
| PSEATVYLPPVPVSKVVSTD | (SEQ ID NO 3), |
| VSTDEYVARTNIYYHAGTS | (SEQ ID NO 4), |
| HAGTSRLLAVGHPYFPIKKP | (SEQ ID NO 5), |
| SGLQYRVFRIHLPDPNKFGF | (SEQ ID NO 7), |
| NKFGFPDTSFYNPDTQRLVW | (SEQ ID NO 8), |
| QRLVWACVGVEVGRGQPLGV | (SEQ ID NO 9), |
| VDNRECISMDYKQTQLCLIG | (SEQ ID NO 12), |
| LCLIGCKPPIGEHWGKGSPC | (SEQ ID NO 13), |
| KGSPCTNVAVNPGDCPPLEL | (SEQ ID NO 14), |
| PPLELINTVIQDGDMVHTGF | (SEQ ID NO 15), |
| VHTGFGAMDFTTLQANKSEV | (SEQ ID NO 16), |
| NKSEVPLDICTSICKYPDYI | (SEQ ID NO 17), |
| YPDYIKMVSEPYGDSLFFYL | (SEQ ID NO 18), |
| YIKGSGSTANLASSNYFPTP | (SEQ ID NO 21), |
| YFPTPSGSMVTSDAQIFNKP | (SEQ ID NO 22), |
| NGICWGNQLFVTVVDTTRST | (SEQ ID NO 24), |
| SETTYKNTNFKEYLRHGEEY | (SEQ ID NO 26), |
| ACQKHTPPAPKEDDPLKKYT | (SEQ ID NO 31), |
| LKKYTFWEVNLKEKFSADLD | (SEQ ID NO 32), |
| QAGLKAKPKFTLGKRKATPT | (SEQ ID NO 34), |
| QLYKTCKQAGTCPPDIIPKV | (SEQ ID NO 37), |
| IIPKVEGKTIAEQILQYGSM | (SEQ ID NO 38), |
| PMDTFIVSTNPNTVTSSTPI | (SEQ ID NO 49), |
| and | |

GKSIGAKVHYYYDLSTIDPA (SEQ ID NO 57), which is immunoreactive with antibodies to the late protein peptide, as determined by competitive immunoassay, in an animal or human infected with papillomavirus, wherein the formation of mammalian antibody/antigen complex is a confirmation for the presence of an infection with papillomavirus.

33. A method as in claim 32, wherein said IgA antibody-antigen complex is of human origin and the infection to be detected is HPV infection or HPV-associated disease.

34. A method as in claim 32, wherein the presence of said complex is ascertained by immunoassay.

35. A method as in claim 34, wherein the immunoassay is ELISA.

36. A method as in claim 34, wherein the immunoassay is immunoblotting.

37. A method as in claim 32, wherein the detection is effected on a secretion.

38. A method as in claim 37, wherein the detection is effected on cervical secretion.

39. A method as in claim 38, wherein the detection is made for diagnosis of cervical neoplasia.

40. A method as in claim 37, wherein the secretion is taken on a swab, brush, or spatula, and is washed off therefrom in a liquid diluent.

41. A method as in claim 32, wherein the detection is effected on serum.

* * * * *